United States Patent [19]

Schütze et al.

[11] Patent Number: 5,380,852
[45] Date of Patent: Jan. 10, 1995

[54] 5-CHLOROQUINOLIN-8-OXYALKANECARBOXYLIC ACID DERIVATIVES, USEFUL AS ANTIDOTES FOR HERBICIDES

[75] Inventors: Rainer Schütze, Kelkheim;
Heinz-Josef Löher, Liederbach;
Frank Ziemer, Frankfurt am Main;
Klaus Bauer, Hanau; Hermann Bieringer, Eppstein/Taunus, all of Germany

[73] Assignee: Hoechst Atkiengesellschaft, Frankfurt am Main, Germany

[21] Appl. No.: 810,487

[22] Filed: Dec. 19, 1991

[30] Foreign Application Priority Data

Dec. 21, 1990 [DE] Germany ............... 4041121

[51] Int. Cl.$^6$ ............... C07D 215/28
[52] U.S. Cl. ............... 546/174; 546/175; 546/176; 546/177; 546/178; 546/180; 504/247
[58] Field of Search ............... 546/174, 175

[56] References Cited

U.S. PATENT DOCUMENTS

| | | | |
|---|---|---|---|
| 1,587,073 | 6/1926 | Hahl | 546/178 |
| 3,133,810 | 5/1964 | Hamm | 71/2.7 |
| 3,351,525 | 11/1967 | Hodel | 167/53.1 |
| 4,188,487 | 2/1980 | Los | 548/301 |
| 4,602,923 | 7/1986 | Handte et al. | 71/88 |
| 4,623,727 | 11/1986 | Hubele | 546/178 |
| 4,749,406 | 6/1988 | Martin . | |
| 4,851,031 | 7/1989 | Bellucci et al. | 71/92 |
| 4,881,966 | 11/1989 | Nyffeler et al. | 71/94 |
| 4,902,340 | 2/1990 | Hubele | 71/94 |
| 5,102,445 | 4/1992 | Hubele | 71/94 |

FOREIGN PATENT DOCUMENTS

| | | |
|---|---|---|
| 0094349 | 11/1983 | European Pat. Off. . |
| 0138773 | 4/1985 | European Pat. Off. . |
| 159287 | 10/1985 | European Pat. Off. . |
| 0159290 | 10/1985 | European Pat. Off. . |
| 0191736 | 8/1986 | European Pat. Off. . |
| 0258184 | 3/1988 | European Pat. Off. . |
| 2546845 | 9/1977 | Germany . |

OTHER PUBLICATIONS

European Search Report EP 91121622 Oct. 5, 1992.

Primary Examiner—David B. Springer
Attorney, Agent, or Firm—Curtis, Morris & Safford

[57] ABSTRACT

Disclosed are compounds of the formula (I):

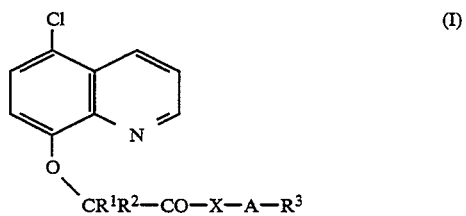

The substituents are disclosed in the specification. The compounds are herbicidal safenets. Accordingly, processes for the preparation and use of the compounds of formula (I) are also disclosed.

14 Claims, No Drawings

5-CHLOROQUINOLIN-8-OXYALKANECARBOXYLIC ACID DERIVATIVES, USEFUL AS ANTIDOTES FOR HERBICIDES

DESCRIPTION

The invention relates to the technical field of plant protection agents, specifically to antidotes or safeners for protecting crop plants against the undesirable side effects of herbicides.

It is already known that compounds from the quinolinoxyalkanecarboxylic acid derivative series can be employed as antidotes or safeners together with herbicides (see, for example, EP-A-94 349 (U.S. Pat. No. 4,902,340), EP-A-191 736 (U.S. Pat. No. 4,881,966), EP-A-0159287 (U.S. Pat. No. 4,851,031), DE-A25 46 845 and EP-A-159 290). However, it has emerged that the known compounds have disadvantages in their application technology, for example they have too low a safener action or reduce the action of the herbicides against harmful plants in an undesirable manner.

The invention relates to novel 5-chloroquinolin-8-oxyalkanecarboxylic acid derivatives of the formula I

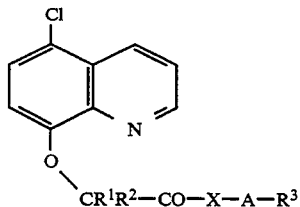

in which $R^1$ and $R^2$ independently of one another are hydrogen or $(C_1-C_4)$-alkyl, preferably hydrogen or methyl, X is an oxygen or sulfur atom or $NR^4$, in which $R^4$ is hydrogen, $(C_1-C_6)$-alkyl, $(C_1-C_6)$-alkoxy or optionally substituted phenyl, preferably O, NH or $NCH_3$, in particular O, A is $(C_1-C_6)$-alkylene, $(C_1-C_8)$-alkenylene, $(C_1-C_8)$-alkynylene, $(C_3-C_8)$-cycloalkylene or $(C_3-C_8)$-cycloalkenylene and $R^3$ is $(C_1-C_6)$-alkenyloxy, $(C_1-C_6)$-alkynyloxy, phenyl-$(C_1-C_4)$-alkoxy, in which the phenyl ring is unsubstituted or substituted by one or more radicals from the group comprising halogen, nitro, $(C_1-C_4)$-alkyl, $(C_1-C_4)$-alkoxy, $(C_1-C_4)$-haloalkyl and $(C_1-C_4)$-haloalkoxy, $R^5R^6R^7Si$—, $R^5R^6R^7Si$—O—, $R^5R^6R^7Si$—$(C_1-C_4)$ -alkoxy, $(C_3-C_6)$ -alkenyloxycarbonyl, $(C_3-C_6)$ -alkynyloxycarbonyl, phenyl-$(C-C_4)$ -alkoxycarbonyl, in which the phenyl ring is unsubstituted or substituted by one or more radicals from the group comprising halogen, nitro, $(C_1-C_4)$-alkyl, $(C_1-C_4)$ -alkoxy, $(C_1-C_4)$ -haloalkyl and $(C_1-C_4)$-haloalkoxy, $R^{56}C=N$—O—CO—, $R^5R^6C=N$—O—, $R^5R^6N$—O—, $R^5R^6C=N$—, $(C_2-C_6)$-alkenylcarbonyl, $(C_2-C_6)$-alkynylcarbonyl, 1-(hydroxyimino)-$(C_1-C_6)$-alkyl, 1-[$(C_1-C_4)$-alkylimino]-$(C_1-C_6)$-alkyl, 1-[$(C_1-C_4)$-alkoxyimino]-$(C_1-C_6)$-alkyl, a radical of the formula $R^8O$—$CH(OR^9)$- or $R^8O$—$CH(OR^9)$—$(CH_2)_n$—O—, in which n is 0, 1 or 2, or an alkoxy radical of the formula $R^8O$—$CHR^{10}$—$CH(OR^9)$—$(C_1-C_4)$-alkoxy, $(C_1-C_6)$-alkylcarbonyloxy in which alkyl is unsubstituted or substituted by halogen, nitro, optionally substituted phenyl or $(C_1-C_4)$-alkoxy, $(C_2-C_6)$ -alkenylcarbonyloxy, $(C_1-C_6)$-alkynylcarbonyloxy, $(C_1-C_6)$-alkylcarbonylamino, $(C_2-C_6$-alkenylcarbonylamino, $(C_2-C_6)$-alkynylcarbonylamino, phenylcarbonyloxy, phenylcarbonylamino, phenyl-$(C_1-C_4)$-alkylcarbonylamino, phenyl in the last three radicals mentioned being in each case unsubstituted or substituted by one or more radicals from the group comprising halogen, nitro, $(C_1-C_4)$-alkyl, $(C_1-C_4)$-alkoxy, $(C_1-C_4)$-haloalkyl and $(C_1-C_4)$ -haloalkoxy, aminocarbonyl, $(C_1-C_6)$-alkylaminocarbonyl, $(C_1-C_6)$-dialkylaminocarbonyl, $(C_3-C_6)$-alkenylaminocarbonyl, $(C_3-C_6)$-alkynylaminocarbonyl, $(C_1-C_6)$-alkoxycarbonylamino, $(C_1-C_6)$-alkylaminocarbonylamino or $(C_1-C_6)$-alkylthiocarbonyl, $(C_3-C_8)$ -alkenylthio or $(C_3-C_6)$ -alkynylthio, $R^5$, $R^6$ and $R^7$ independently of one another are H, $(C_1-C_4)$-alkyl or optionally substituted phenyl, or $R^5$ and $R^6$, together with the nitrogen or carbon atom Joining them, are a ring having 3 to 7 ring atoms, preferably 5 or 6 ring atoms, which is unsubstituted or substituted by $(C_1-C_4)$-alkyl or $(C_1-C_4)$-alkoxy, $R^8$ and $R^9$ independently of one another are $(C_1-C_4)$-alkyl, or $R^8$ and $R^9$ together are a straight-chain or branched $(C_1-C_4)$ -alkylene bridge and $R^{10}$ is hydrogen or $(C_1-C_4)$-alkyl.

In the formulae, alkyl, alkenyl and alkynyl are straight-chain or branched; the same applies to substituted alkyl, alkenyl and alkynyl radicals, such as haloalkyl, hydroxyalkyl, alkoxycarbonyl and the like; alkyl is, for example, methyl, ethyl, n- or i-propyl, n-, i-, t- or 2-butyl, pentyl radicals, hexyl radicals, such as n-hexyl, i-hexyl or 1,3-dimethylbutyl, or heptyl radicals, such as n-heptyl, 1-methylhexyl or 1,4-dimethylpentyl; alkenyl is, for example, allyl, 1-methylprop-2-en-1-yl, 2-methylprop-2-en-1-yl, but-2-en-1-yl, but-3-en-1-yl, 1-methylbut-3-ene or 1-methyl-but-2-ene; alkynyl is, for example, propargyl, but-2-yn-1-yl, but-3-yn-1-yl or 1-methyl-but-3-yne; halogen is fluorine, chlorine, bromine or iodine, preferably fluorine, chlorine or bromine, in particular fluorine or chlorine; haloalkyl, -alkenyl and -alkynyl are alkyl, alkenyl or alkynyl substituted by halogen, for example $CF_3$, $CHF_2$, $CH_2F$, $CF_3CF_2$, $CH_2FCHCl$, $CCl_3$, $CHCl_2$ or $CH_2CH_2Cl$; haloalkoxy is, for example, $OCF_3$, $OCHF_2$, $OCH_2F$, $CF_3CF_2O$ or $OCH_2CF_3$; and optionally substituted phenyl is, for example, phenyl which is unsubstituted or substituted by one or more radicals from the group comprising halogen, $(C_1-C_4)$-alkyl, $(C_1-C_4)$-alkoxy, $(C_1-C_4)$-halogenoalkyl, $(C_1-C_4)$-halogenoalkoxy and nitro, for example o-, m- or p-tolyl, dimethylphenyl radicals, 2-, 3- or 4-chlorophenyl, 2-, 3- or 4-trifluoro- or -trichlorophenyl, 2,4- 3,5-, 2,5- or 2,3-dichlorophenyl, and o-, m- or p-methoxyphenyl.

Some compounds of the formula I contain one or more asymmetric C atoms or double bonds which are not shown separately in the general formula I. However, formula I includes all the possible stereoisomers defined by their specific spatial form, such as enantiomers, diastereomers and E- and Z-isomers, and mixtures thereof. The pure or enriched stereoisomers can be obtained from mixtures of the stereoisomers by customary methods, or can also be prepared from stereochemically pure starting substances by stereoselective reactions. This invention thus relates to the stereoisomers mentioned in the pure form and also their mixtures.

Compounds of the formula (I) according to the invention which are of particular interest are those in which $R^3$ is $(C_3-C_4)$ -alkenyloxy, $(C_3-C_4)$ -alkynyloxy, phenyl- $(C_1-C_2)$-alkoxy, in which the phenyl ring is unsubstituted or substituted by one or more radicals from the group comprising halogen, nitro, $(C_1-C_2)$-alkyl, $(C_1-C_2)$-alkoxy, $(C_1-C_2)$-haloalkyl and $(C_1-C_2)$-haloalkoxy, $R^5R^6R^7Si-$, $R^5R^6R^7Si-O-$, $R^5R^6R^7Si-(C_1-C_2)$-alkoxy, $(C_3-C_4)$-alkenyloxycarbonyl, $(C_3-C_4)$-alkynyloxycarbonyl, phenyl-$(C_1-C_2)$-alkoxycarbonyl, in which the phenyl ring is unsubstituted or substituted by one or more radicals from the group comprising halogen, nitro, $(C_1-C_2)$-alkyl, $(C_1-C_2)$-alkoxy, $(C_1-C_2)$-haloalkyl and $(C_1-C_2)$-haloalkoxy, $R^5R^6C=N-O-CO-$, $R^5R^6C=N-O-$, $R^5R^6N-O-$, $R^5R^6C=N-$, $(C_2-C_4)$-alkenylcarbonyl, $(C_2-C_4)$-alkynylcarbonyl, 1-(hydroxyimino)-$(C_1-C_4)$-alkyl, 1-[$(C_1-C_4)$-alkylimino]-$(C_1-C_4)$-alkyl, 1-[$(C_1-C_4)$-alkoxyimino]-$(C_1-C_4)$-alkyl, $R^8O-CH(OR^9)$-$(C_1-C_5)$-alkyl, $(C_1-C_4)$-alkylcarbonyloxy, $(C_3-C_4)$-alkenylcarbonyloxy, $(C_3-C_4)$-alkynylcarbonyloxy, $(C_1-C_4)$-alkylcarbonylamino, $(C_3-C_4)$-alkenylcarbonylamino, $(C_3-C_4)$-alkynylcarbonylamino, phenylcarbonyloxy, phenylcarbonylamino, phenyl-$(C_1-C_2)$-alkylcarbonylamino, phenyl in the last three radicals mentioned being optionally substituted, $(C_1-C_4)$-alkylaminocarbonyl, di-$(C_1-C_4)$-alkylaminocarbonyl, $(C_3-C_4)$-alkenylaminocarbonyl, $(C_1-C_4)$-alkylthiocarbonyl, $(C_3-C_4)$-alkenylthio, $(C_1-C_4)$-alkoxycarbonylamino, $(C_1-C_4)$-alkylaminocarbonylamino or a radical of the formula $-O-CH_2-CH(OR')-CH_2-OR'$, in which the radicals R' together represent the divalent group $CH_2$, $CHCH_3$ or $C(CH_3)_2$, $R^5$, $R^6$ and $R^7$ independently of one another are H or $(C_1-C_2)$-alkyl, or $R^5$ and $R^6$, together with the nitrogen or carbon atom joining them, form a ring having 3 to 7 ring atoms, preferably 5 or 6 ring atoms, and $R^8$ and $R^9$ independently of one another are $(C_1-C_4)$-alkyl.

Preferably, $R^3$ is $(C_3-C_4)$-alkenyloxy, $(C_3-C_4)$-alkynyloxy, benzyloxy, trimethylsilyl, triethylsilyl, trimethylsilylmethoxy, 1-(hydroxyimino)-$(C_1-C_4)$-alkyl, 1-[$(C_1-C_4)$-alkylimino]-$(C_1-C_4)$-alkyl, 1-[$(C_1-C_4)$-alkoxyimino]-$(C_1-C_4)$-alkyl, $(C_3-C_4)$-alkenyloxycarbonyl, $(C_3-C_4)$-alkynyloxycarbonyl or $R^5R^6C=N-O-$, in which $R^5$ and $R^6$, in the last radical mentioned, independently of one another are methyl or ethyl or, together with the carbon atom joining them, are cyclopentylidene or cyclohexylidene.

Preferably,

A is $(C_1-C_4)$-alkylene or $(C_4-C_5)$-alkenylene, in particular $CH_2CH_2$, $CH(CH_3)CH_2$, $C(CH_3)_2CH_2$ or $CH(CH_3)CH(CH_3)$.

Particularly preferably, the group $-A-R^3$ is $(C_3-C_4)$-alkenyloxy-$(C_2-C_4)$-alkyl, $(C_3-C_4)$-alkynyloxy-$(C_2-C_4)$-alkyl, benzyloxy-$(C_2-C_4)$-alkyl, trimethylsilyl-$(C_1-C_4)$-alkyl, $-(C_2-C_4)$-alkenyl or $-(C_2-C_4)$-alkynyl, triethylsilyl-$(C_1-C_4)$-alkyl, $-(C_2-C_4)$-alkenyl or $-(C_2-C_4)$-alkynyl, trimethylsilylmethoxy-$(C_1-C_4)$-alkyl, $(C_3-C_4)$-alkenyloxycarbonyl-$(C_1-C_4)$-alkyl, $(C_3-C_4)$-alkynyloxycarbonyl-$(C_1-C_4)$-alkyl or $R^5R^6C=N-O-(C_2-C_4)$-alkyl, in which $R^5$ and $R^6$, in the last radical mentioned, independently of one another are methyl or ethyl or, together with the carbon atom joining them, are cyclopentylidene or cyclohexylidene.

Preferred compounds of the formula I according to the invention are those in which the group of the formula $-A-R^3$ is 2-(allyloxy)-ethyl, 3-(allyloxy)-n-propyl, 4-(allyloxy)-n-butyl, 2-(allyloxy)-1-methyl-ethyl, 2-(2-methylprop-2-en-1-yl)-ethyl, 2-(propargyloxy)-ethyl, 2-(propargyloxy)-1-methyl-ethyl, 3-propargyloxy-propyl, 4-propargyloxybutyl, 2-benzyloxyethyl, allyloxycarbonylmethyl, 1-(allyloxycarbonyl)-1-ethyl, 1-(allyloxycarbonyl)-1,1-dimethylmethyl, propargyloxycarbonylmethyl, 1-(propargyl-oxycarbonyl)-1-ethyl, 3-trimethylsilyl-prop-2-en-1-yl, 3-trimethylsilyl-prop-2-yn-1-yl, 3-trimethylsilyl-1-methyl-prop-2-yn-1-yl, 3-trimethylsilyl-1,1-dimethyl-prop-2-yn-1-yl, trimethylsilylmethoxycarbonylmethyl, trimethylsilylmethoxyethyl, trimethylsiloxyethyl, cyclohexylideneaminoxyethyl or -1-(methyl)-ethyl, cyclopentylideneaminooxyethyl or -1-(methyl)-ethyl, 2-propylideneaminooxyethyl or -1-(methyl)-ethyl, 3-pentylideneaminooxyethyl or -1-(methyl)-ethyl, 2-propylideneaminooxycarbonylmethyl or (2,2-dimethyl-1,3-dioxolan-4-yl)-methyl.

The invention also relates to a process for the preparation of the compounds of the formula I according to the invention, which comprises a) reacting 5-chloro-8-hydroxyquinoline with an alkanecarboxylic acid derivative of the formula II $$Y-CR^1R^2-CO-X-A-R^3 \qquad \text{II}$$

in which

Y is a leaving group, such as, for example, chlorine, bromine, methanesulfonyl or toluenesulfonyl and $R^1$, $R^2$, $R^3$, X and A are as defined for the above formula I, or b) reacting 5-chloroquinolin-8-oxy-alkanecarboxylic acids of the formula I in which $-X-A-R^3$ is replaced by hydroxyl with alcohols, mercaptans or amines of the formula $$H-X-A-R^3$$

in which X, A and $R^s$ are as defined for formula I.

The 5-chloroquinolin-8-oxy-alkanecarboxylic acids employed in variant b) are obtained, for example, from the ethyl ester, which can be prepared by variant a), by alkaline hydrolysis.

The reaction of the compound II with 5-chloro-8-hydroxyquinoline according to variant a) is preferably carried out in dipolar aprotic solvents, such as dimethylsulfoxide or N,N-dimethylformamide, at elevated temperature, in particular between 80° and 120° C., in the presence of a base, in particular alkali metal carbonates, such as, for example, potassium carbonate.

The reaction according to variant b) is preferably carried out in dipolar aprotic solvents, in particular ethers, such as, for example, tetrahydrofuran or 1,4-dioxane, or halogenohydrocarbons, such as, for example, chloroform or carbon tetrachloride, in the presence of a reagent which converts the carboxyl group into an activated derivative, such as, for example, thionyl chloride, N,N'-carbonyldiimidazole or dicyclohexylcarbodiimide, at temperatures from room temperature up to the boiling point of the reaction mixture, in particular at the reflux temperature.

5-Chloro-8-hydroxyquinoline is commercially obtainable. The bromoalkanecarboxylic acid derivatives of the formula II can be prepared by processes which are known in the literature from bromoalkanecarboxylic acid chlorides and compounds of the formula H-X-A-R^3, in which X, A and $R^3$ are as defined in formula I. Alcohols, mercaptans or amines of the formula $H-X-A-R^3$ are accessible by processes which are known from the literature, if they are not also commercially obtainable; see, for example, Helv. Chim Acta 67, page 1470 et seq. (1984); J. Am. Chem. Soc. 71, pages 1152 et seq. (1949); *J. Am. Chem. Soc.* 60, pages 1472 et seq. (1938); U.S. Pat. No. 3,123,639 and EP-A-52 798.

Compounds of the formula I reduce or suppress phytotoxic side effects of herbicides which may occur when the herbicides are used in crops of useful plants, and can therefore be called antidotes or safeners in the customary manner.

The compounds of the formula I according to the invention can be applied together with herbicidal active compounds or in any desired sequence, and are then capable of reducing or completely eliminating harmful side effects of these herbicides on crop plants, without impairing the activity of these herbicides against harmful plants.

The field of use of conventional plant protection agents can be extended quite considerably by these compounds. Herbicides of which the phytotoxic side effects on crop plants can be reduced by means of compounds of the formula I are, for example, carbamates, thiocarbamates, halogenoacetanilides, substituted phenoxy-, naphthoxy and phenoxy-phenoxycarboxylic acid derivatives as well as heteroaryloxyphenoxyalkanecarboxylic acid derivatives, such as quinolyloxy-, quinoxalyloxy-, pyridyloxy-, benzoxalyloxy- and benzothiazolyloxy-phenoxyalkanecarboxylic acid esters, cyclohexanedione derivatives, imidazolinones and sulfonylureas. Preferred compounds here are phenoxy-phenoxy- and heteroaryloxy-phenoxycarboxylic acid esters and salts, sulfonylureas and imidazolinones.

Examples of suitable herbicides which can be combined with the safeners according to the invention are:

A) Herbicides of the phenoxyphenoxy- and heteroaryl phenoxycarboxylic acid ($C_1$–$C_4$)alkyl, ($C_2$–$C_4$)alkenyl and ($C_3$–$C_4$) alkynyl ester type, such as A1) phenoxyphenoxy- and benzyloxy-phenoxy-carboxylic acid derivatives, for example methyl 2-(4-(2,4-dichlorophenoxy)-phenoxy)-propionate (diclofop-methyl), methyl 2-(4-(4-bromo-2-chlorophenoxy)-phenoxy)-propionate (see DE-A-2601548), methyl 2-(4-(4-bromo-2-fluorophenoxy)-phenoxy)-propionate (see U.S. Pat. No. 4808750), methyl 2-(4-(2-chloro-4-trifluoromethylphenoxy)-phenoxy)propionate (see DE-A-2433067), methyl 2-(4-(2-fluoro-4-trifluoromethylphenoxy)-phenoxy)propionate (see U.S. Pat. No. 4808750), methyl 2-(4-(2,4-dichlorobenzyl)-phenoxy)propionate (see DE-A-2417487), ethyl 4-(4-(4-trifluoromethylphenoxy)-phenoxy)-pent-2-enoate and methyl 2-(4-(4-trifluoromethylphenoxy)-phenoxy)-propionate (see DE-A-2433067), A2) "mononuclear" heteroaryloxy-phenoxy-alkanecarboxylic acid derivatives, for example ethyl 2-(4-(3,5-dichloropyridyl-2-oxy)-phenoxy)-propionate (see EP-A-2925), propargyl 2-(4-(3,5-dichloropyridyl-2-oxy)-phenoxy)propionate (EP-A-3114), methyl 2-(4-(3-chloro-5-trifluoromethyl-2-pyridyloxy)-phenoxy-propionate (see EP-A-3890), ethyl 2-(4-(3-chloro-5-trifluoromethyl-2-pyridyloxy)-phenoxy)-propionate (see EP-A-3890), propargyl 2-(4-(5-chloro-3-fluoro-2-pyridyloxy)-phenoxy)propionate (EP-A-191736) and butyl 2-(4-(5-trifluoromethyl-2-pyridyloxy)-phenoxy)propionate (fluazifop-butyl), A3) "dinuclear" heteroaryloxy-phenoxy-alkanecarboxylic acid derivatives, for example methyl and ethyl 2-(4-(6-chloro-2-quinoxalyloxy)-phenoxy)-propionate (quizalofop-methyl and -ethyl), methyl 2-(4-(6-fluoro-2-quinoxalyloxy)-phenoxy)-propionate (see J. Pest. Sci. Volume 10, 61 (1985)), 2-(4-(6-chloro-2-quinoxalyloxy)-phenoxy)-propionic acid and its methyl ester and tetrahydrofurfuryl and 2-isopropylideneaminooxyethyl ester (propaquizafop and diverse esters), ethyl 2-(4-(6-chlorobenzoxazol-2-yl-oxy)-phenoxy)-propionate (fenoxaprop-ethyl) and ethyl 2-(4-(6-chlorobenzothiazol-2-yloxy)phenoxy-propionate (see DE-A-2640730).

B) Herbicides from the sulfonylurea series, such as, for example, pyrimidine- or triazinylaminocarbonyl-[benzene, pyridine, pyrazole, thiophene and (alkylsulfonyl)alkylamino]-sulfamides. Preferred substituents on the pyrimidine ring or triazine ring are alkoxy, alkyl, haloalkoxy, haloalkyl, halogen or dimethylamino, it being possible for all the substituents to becombined, independently of one another. Preferred substituents in the benzene, pyridine, pyrazole, thiophene or (alkylsulfonyl)alkylamino part are alkyl, alkoxy, halogen, nitro, alkoxycarbonyl, aminocarbonyl, alkylaminocarbonyl, dialkylaminocarbonyl, alkoxyaminocarbonyl, alkyl, alkoxyaminocarbonyl, haloalkoxy, haloalkyl, alkylcarbonyl, alkoxyalkyl and (alkanesulfonyl)alkylamino. Examples of suitable sulfonylureas are B1) phenyl- and benzylsulfonylureas and related compounds, for example 1-(2-chlorophenylsulfonyl)-3-(4-methoxy-6-methyl-1,3,5-triazin-2-yl)urea (chlorsulfuron), 1-(2-ethoxycarbonylphenylsulfonyl)-3-(4-chloro-6-methoxypyrimidin-2-yl)urea (chlorimuron-ethyl), 1-(2-methoxyphenylsulfonyl)-3-(4-methoxy-6-methyl-1,3,5-triazin-2-yl)urea (metsulfuron-methyl), 1-(2-chloroethoxy-phenylsulfonyl)-3-(4-methoxy-6-methyl-1,3,5-triazin-2-yl)urea (triasulfuron), 1-(2-methoxycarbonyl-phenylsulfonyl)-3-(4,6-dimethylpyrimidin-2-yl)urea (sulfometuron-methyl), 1-(2-methoxycarbonylphenylsulfonyl)-3-(4-methoxy-6-methyl-1,3,5-triazin-2-yl)-3-methylurea (tribenuron-methyl), 1-(2-methoxycarbonylbenzylsulfonyl)-3-(4,6-dimethoxypyrimidin-2-yl)urea (bensulfuron-methyl), 1-(2-methoxycarbonylphenylsulfonyl)-3-(4,6-difluoromethoxy)pyrimidin-2-yl)urea (primisulfuron-methyl), 3-(4-ethyl-6-methoxy-1,3,5-triazin-2-yl)-1-(2,3-dihydro-1,1-dioxo-2-methylbenzo[b]thiophene-7-sulfonyl)-urea (see EP-A-79683) and 3-(4-ethoxy-6-ethyl-1,3,5-triazin-2-yl)-1-(2,3-dihydro-1,1-dioxo-2-methylbenzo[b]thiophene-7-sulfonyl)-urea (see EP-A-79683), B2) thienylsulfonylureas, for example 1-(2-methoxycarbonyl thiophen-3-yl)-3-(4-methoxy-6-methyl-1,3,5-triazin-2-yl)urea (thifensulfuron-methyl), B3) pyrazolylsulfonylureas, for example 1-(4-ethoxycarbonyl-1-methylpyrazol-5-yl-sulfonyl)-3-(4,6-dimethoxypyrimidin-2-yl)urea (pyrazosulfuron-methyl) and methyl 3-chloro-5-(4,6-dimethoxypyrimidin-2-ylcarbamoylsulfamoyl)-1-methyl-pyrazol-4-carboxylate (see EP 282613), B4) sulfonyldiamide derivatives, for example 3-(4,6-dimethoxypyrimidin-2-yl)-1-(N-methyl-N-methylsulfonylaminosulfonyl)urea (amidosulfuron) and structural analogs ( see EP-A-0131258 and Z. Pfl. Krankh. Pfl.

Schutz, Special edition XII, 489–497 (1990)),

B5) pyridylsulfonylureas, for example
1-(3-N,N-dimethylaminocarbonylpyridin-2-yl-sulfonyl)-3-(4,6-dimethoxypyrimidin-2-yl)urea (nicosulfuron), 1-(3-ethylsulfonylpyridin-2-yl-sulfonyl)-3-(4,6-dimethoxy-pyrimidin-2-yl)urea (DPX-E 9636, see Brighton Crop Prot. Conf.—Weeds—1989, page 23 et seq.) and pyridylsulfonylureas, such as those described in WO 91/10660 and German Patent Application P 4030577.5, preferably those of the formula III or the salts thereof

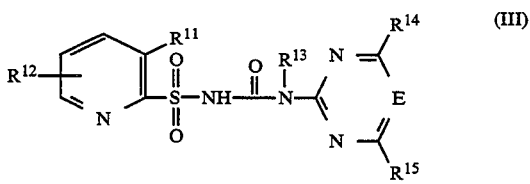

in which

E is CH or N, preferably CH, $R^{11}$ is iodine or $NR^{16}R^{17}$, $R^{12}$ is H, halogen, cyano, $C_1$–$C_3$-alkyl, $C_1$–$C_3$-alkoxy, $C_1$–$C_3$-haloalkyl, $C_1$–$C_3$-haloalkoxy, $C_1$–$C_3$-alkylthio, ($C_1$–$C_3$-alkoxy)-$C_1$–$C_3$-alkyl, ($C_1$–$C_3$-alkoxy)-carbonyl, mono- or di- ($C_1$–$C_3$-alkyl)-amino, $C_1$–$C_3$-alkylsulfinyl or -sulfonyl, SO—$NR^aR^b$ or CO—$NR^aR^b$, in particular H, $R^a$ and $R^b$ independently of one another are H, $C_1$–$C_3$-alkyl, $C_1$–$C_3$-alkenyl or $C_1$–$C_3$-alkynyl, or together are —$(CH_2)_4$—, —$(CH_2)_5$— or —$(CH_2)_2$—O—$(CH_2)_2$—, $R^{13}$ is H or $CH_3$, $R^{14}$ is halogen, $C_1$–$C_2$-alkyl, $C_1$–$C_2$-alkoxy, $C_1$–$C_2$-haloalkyl, preferably $CF_3$, or $C_1$–$C_2$-haloalkoxy, preferably $OCHF_2$ or $OCH_2CF_3$, $R^{15}$ is $C_1$–$C_2$-alkyl, $C_1$–$C_2$-haloalkoxy, preferably $OCHF_2$, or $C_1$–$C_2$-alkoxy, and $R^{16}$ is $C_1$–$C_4$-alkyl and $R^{17}$ is $C_1$–$C_4$-alkylsulfonyl, or $R^{16}$ and $R^{17}$ together are a chain of the formula —$(CH_2)_3SO_2$—or —$(CH_2)_4SO_2$—, for example 3-(4,6-dimethoxypyrimidin-2-yl)-1-(3-N-methylsulfonyl-N-methylaminopyridin-2-yl) sulfonylurea, B6) alkoxyphenoxysulfonylureas, such as those described in EP-A-0342569, preferably those of the formula IV or salts thereof,

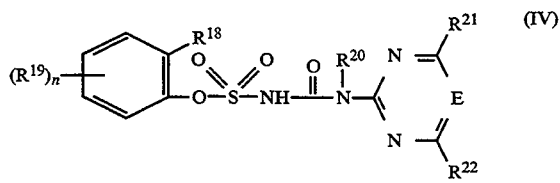

in which

E is CH or N, preferably CH, $R^{18}$ is ethoxy, propoxy or isopropoxy, $R^{19}$ is hydrogen, halogen, $NO_2$, $CF_3$, CN, $C_1$–$C_4$-alkyl, $C_1$–$C_4$-alkoxy, $C_1$–$C_4$-alkylthio or ($C_1$–$C_3$-alkoxy)-carbonyl, preferably in the 6-position on the phenyl ring, n is 1, 2 or 3, preferably 1, $R^{20}$ is hydrogen, $C_1$–$C_4$-alkyl or $C_1$–$C_4$-alkenyl and $R^{21}$ and $R^{22}$ independently of one another are halogen, $C_1$–$C_2$-alkyl, $C_1$–$C_2$-alkoxy, $C_1$–$C_2$-haloalkyl, $C_1$–$C_2$-haloalkoxy or ($C_1$–$C_2$-alkoxy)-$C_1$–$C_2$-alkyl, preferably $OCH_3$ or $CH_3$, for example 3-(4,6-dimethoxypyrimidin-2-yl)-1-(2-ethoxyphenoxy)-sulfonylurea, and other related sulfonylurea derivatives and mixtures thereof;

C) Chloroacetanilide herbicides, such as
N-methoxymethyl-2,6-diethyl-chloroacetanilide (alachlor), N-(3'-methoxyprop-2'-yl)-2-methyl-6-ethyl-chloroacetanilide (metolachlor), N-(3-methyl-1,2,4-oxdiazol-5-yl-methyl)-chloroacetic acid 2,6-dimethylanilide and N-(2,6-dimethylphenyl)-N-(1-pyrazolylmethyl)-chloroacetamide (metazachlor);

D) Thiocarbamates, such as S-ethyl N,N-dipropylthiocarbamate (EPTC) or S-ethyl N,N-diisobutylthiocarbamate (butylate);

E) Cyclohexanedione derivatives, such as methyl 3-(1-allyloxyimino)butyl)-4-hydroxy-6,6-dimethyl-2-oxycyclohex-3-enecarboxylate (alloxydim), 2-(N-ethoxybutyrimidoyl)-5-(2-ethylthiopropyl)-3-hydroxy-2-cyclohexen-1-one (sethoxydim), 2-(N-ethoxybutyrimidoyl)-5-(2-phenylthiopropyl)-3-hydroxy-2-cyclohexen-1-one (cloproxydim), 2-(1-(3-chloroallyloxy)iminobutyl)-5-(2-ethylthio)-propyl)-3-hydroxy-2-cyclohexen-1-one, 2-(1-(3-chloroallyloxy)iminopropyl)-5-(2-ethylthio)-propyl)-3-hydroxy-cyclohex-2-enone (clethodim), 2-(1-allyloxyiminobutyl)-4-methoxycarbonyl-5,5-dimethyl-3-oxocyclohexenol, 2-(1-(ethoxyimino)-butyl)-3-hydroxy-5-(thian-3-yl)-cyclohex-2-enone (cycloxydim) or 2-(1-ethoxyiminopropyl)-5-(2,4,6-trimethylphenyl)-3-hydroxy-2-cyclohexen-1-one (tralkoxydim);

F) 2-Carboxyphenyl- or 2-carboxyheteroaryl-imidazolinones, salts and esters (for example alkyl esters) thereof, for example the mixture of methyl 2-(4-isopropyl-4-methyl-5-oxo-2-imidazolin-2-yl)-5-methylbenzoate and methyl 2-(4-isopropyl-4-methyl-5-oxo-2-imidazolin-2-yl)-4-methylbenzoate (imazamethabenz), 5-ethyl-2-(4-isopropyl-4-methyl-5-oxo-2-imidazolin-2-yl)-pyridine-3-carboxylic acid (imazethapyr), esters and salts (for example the $NH_4$ salt) thereof, 2-(4-isopropyl-4-methyl-5-oxo-2-imidazolin-2-yl)-quinoline-3-carboxylic acid (imazaquin), esters and salts (for example the $NH_4$ salt) thereof, and rac-2-[4,5-dihydro-4-methyl-4-(1-methylethyl)-5-oxo-1H-imidazol-2-yl]-5-methyl-3-pyridine-carboxylic acid (imazethamethapyr) and esters and salts thereof.

The abovementioned herbicides of group A to F are known to the expert and as a rule are described in "The Pesticide Manual", British Crop Protection Council, 9th edition 1991 or 8th edition 1987 or in "Agricultural Chemicals Book II, Herbicides", by W. T. Thompson, Thompson Publications, Fresno Calif., USA 1990 or in "Farm Chemicals Handbook '90", Meister Publishing Company, Willoughby Ohio, USA 1990. Imazethamethapyr is known from Weed Techn. 1991, Volume 5, 430–438.

The herbicidal active compounds and the safeners mentioned can be applied together (as a finished formulation or in the tank-mix process) or successively in any desired sequence. The safener:herbicide weight ratio can vary within wide limits and is preferably in the range from 1:10 to 10:1, in particular 1:10 to 5:1. The particular optimum amounts of herbicide and safener depend on the type of herbicide used or on the safener used and on the nature of the plant stock to be treated, and can be determined from case to case by appropriate preliminary experiments.

The main fields of use for the safeners are, above all, cereal crops (wheat, rye, barley, oats), rice, maize or sorghum, and also cotton and soybean, preferably cereals and maize.

A particular advantage of the safenets of the formula I according to the invention is to be found when they are combined with herbicides from the group comprising sulfonylureas and/or imidazolinones. Herbicides of the structural classes mentioned primarily inhibit the key enzyme acetolactate synthase (ALS) in the plants and are therefore at least partly related in respect of the action mechanism. Some herbicides of these structural classes cannot be employed selectively or selectively enough, specifically in cereal crops and/or maize. By combining them with the safeners according to the invention, outstanding selectivities can also be achieved in cereals or maize with these herbicides.

Depending on their properties, the safeners of the formula I are used for pretreatment of the seed of the crop plants (seed dressing) or are introduced into the seed furrows before sowing or used together with the herbicide before or after emergence of the plants. Pre-emergent treatment includes both treatment of the cultivation area before sowing and treatment of the cultivation areas which have been sown but are not yet covered with growth. Use together with the herbicide is preferred. Tank mixtures or finished formulations can be employed for this purpose.

The application amounts required for the safeners can vary within wide limits, depending on the indication and the herbicide used, and are as a rule in the range from 0.001 to 5 kg, preferably 0.005 to 0.5 kg of active compound per hectare.

The present invention therefore also relates to a method for protecting crop plants against the phytotoxic side effects of herbicides, which comprises applying an effective amount of a compound of the formula I to the plants, plant seeds or cultivation area before, after or at the same time as the herbicide.

The invention also relates to plant protection agents which contain an active compound of the formula I and customary formulation auxiliaries, as well as herbicidal agents which contain an active compound of the formula I and a herbicide as well as formulation auxiliaries customary in the plant protection sector.

The compounds of the formula I and combinations thereof with one or more of the herbicides mentioned can be formulated in various ways, depending on the given biological and/or chemico-physical parameters. Examples of suitable formulation possibilities are: wettable powders (WP), emulsifiable concentrates (EC), water-soluble powders (SP), water-soluble concentrates (SL), concentrated emulsions (EW), such as oil-in-water and water-in-oil emulsions, sprayable solutions or emulsions, capsule suspensions (CS), oil- or water-based dispersions (SC), suspoemulsions, suspension concentrates, dusts (DP), oil-miscible solutions (OL), dressing agents, granules (GR) in the form of microgranules and spray, absorption and adsorption granules, granules for soil application or application by scattering, water-soluble granules (SG), water-dispersible granules (WG), ULV formulations, microcapsules and waxes.

These individual types of formulation are known in principle and are described, for example, in: Winnacker-Küchler, "Chemische Technologie (Chemical Technology)" Volume 7, C. Hauser Verlag Munich, 4th edition 1986; Wade van Valkenburg, "Pesticide Formulations", Marcel Dekker N.Y., 1973; K. Martens, "Spray Drying Handbook", 3rd ed. 1979, G. Goodwin Ltd. London.

The formulation auxiliaries needed, such as inert materials, surfactants, solvents and other additives, are likewise known and are described, for example, in: Watkins, "Handbook of Insecticide Dust Diluents and Carriers", 2nd ed., Darland Books, Caldwell N.J.; H. V. Olphen "Introduction to Clay Colloid Chemistry", 2nd ed., J. Wiley & Sons, N.Y.; Marsden "Solvents Guide", 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte (Surface-Active Ethylene Oxide Adducts)", Wiss. Verlagsgesell., Stuttgart 1976; and Winnacker-Küchler "Chemische Technologie (Chemical Technology)", Volume 7, C. Hauser Verlag Munich, 4th edition 1986.

Combinations with other pesticidally active substances, fertilizers and/or growth regulators can also be prepared, for example in the form of a finished formulation or as a tank mix, on the basis of these formulations.

Wettable powders are preparations which are uniformly dispersible in water and, in addition to the active compound, and apart from a diluent or inert substance, also contain wetting agents, for example polyoxyethylated alkylphenols, polyoxyethylated fatty alcohols and fatty amines, fatty alcohol polyglycol ether-sulfates, alkanesulfonates or alkylarylsulfonates, and dispersing agents, for example sodium ligninsulfonate, sodium 2,2′-dinaphthylmethane-6,6′-disulfonate, sodium dibutylnaphthalenesulfonate or sodium oleyl methyl tauride.

Emulsifiable concentrates are prepared by dissolving the active compound in an organic solvent, for example butanol, cyclohexanone, dimethylformamide, xylene or higher-boiling aromatics or hydrocarbons, with the addition of one or more emulsifiers. Emulsifiers which can be used are, for example: calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products (for example block polymers), alkyl polyethers, sorbitan fatty acid esters, polyoxyethylene sorbitan fatty acid esters or polyoxyethylene sorbitol esters.

Dusts are obtained by grinding the active compound with finely divided solid substances, for example talc, naturally occurring clays, such as kaolin, bentonite and pyrophillite, or diatomaceous earth.

Granules can be prepared either by spraying the active compound onto adsorbent, granular inert material, or by applying actave compound concentrates to the surface of carrier substances, such as sand or kaolinites, or of granular inert material by means of adhesives, for example polyvinyl alcohol, sodium polyacrylate or mineral oils. Suitable active compounds can also be granulated in the manner customary for the preparation of fertilizer granules—if desired as a mixture with fertilizers.

The agrochemical formulations as a rule contain 0.1 to 99 percent by weight, in particular 0.1 to 95% by weight, of active compounds of the formula I (antidote) or of the antidote/herbicide active compound mixture and 1 to 99.9% by weight, in particular 5 to 99.8% by weight, of a solid or liquid additive and 0 to 25% by weight, in particular 0.1 to 25% by weight, of a surfactant.

The active compound concentration in wettable powders is, for example, about 10 to 90% by weight, the remainder to make up 100% by weight consisting of customary formulation constituents. The active compound concentration in emulsifiable concentrates is about 1 to 80% by weight of active compounds. Dust-like formulations contain about 1 to 20% by weight of active compounds, and sprayable solutions about 0.2 to 20% by weight of active compounds. In the case of granules, such as water-dispersible granules, the active compound content depends partly on whether the active compound is present in liquid or solid form. The content in water-dispersible granules is as a rule between 10 and 90% by weight.

The active compound formulations mentioned moreover contain, if appropriate, the particular customary tackifiers, wetting agents, dispersing agents, emulsifiers, penetration agents, solvents, fillers or carriers.

For use, the formulations in the commercially available form are diluted, if appropriate, in the customary manner, for example by means of water in the case of wettable powders, emulsifiable concentrates, dispersions and water-dispersible granules. Dust-like formulations, granules and sprayable solutions are usually not diluted further with additional inert substances before use. The application amount required for the "antidote" varies according to the external conditions, such as temperature, humidity, nature of the herbicide used and the like.

The following examples serve to illustrate the invention:

A. Formulation Examples a) A dust is obtained by mixing 10 parts by weight of a compound of the formula I or an active compound mixture of a herbicide and a compound of the formula I and 90 parts by weight of talc, as the inert substance, and comminuting the mixture in an impact mill.

b) A wettable powder which is readily dispersible in water is obtained by mixing 25 parts by weight of a compound of the formula I or an active compound mixture of a herbicide and a safener of the formula I, 64 parts by weight of kaolin-containing quartz, as the inert substance, 10 parts by weight of potassium ligninsulfonate and 1 part by weight of sodium oleoylmethyl tauride, as the wetting and dispersing agent, and grinding the mixture in a pinned disk mill.

c) A dispersion concentrate which is readily dispersible in water is obtained by mixing 20 parts by weight of a compound of the formula I or an active compound mixture of a herbicide and a safener of the formula I, 6 parts by weight of alkylphenol polyglycol ether ($^R$Triton X 207), 3 parts by weight of isotridecanol polyglycol ether (8 mol of ethylene oxide) and 71 parts by weight of paraffinic mineral oil (boiling range, for example, about 255 to above 277° C.) and grinding the mixture to a fineness of less than 5 microns in a ball mill.

d) An emulsifiable concentrate is obtained from 15 parts by weight of a compound of the formula I or an active compound mixture of a herbicide and a safenet of the formula I, 75 parts by weight of cyclohexanone, as the solvent, and 10 parts by weight of oxyethylated nonylphenol, as the emulsifier.

e) Water-dispersible granules are obtained by mixing

| 75 parts by weight | of a compound of the formula I or an active compound mixture of a herbicide and a safener of the formula I, |
|---|---|
| 10 parts by weight | of calcium ligninsulfonate, |
| 5 parts by weight | of sodium laurylsulfate, |
| 3 parts by weight | of polyvinyl alcohol and |
| 7 parts by weight | of kaolin, | grinding the mixture on a pinned disk mill and granulating the powder in a fluidized bed by spraying on water as the granulating liquid.

f) Water-dispersible granules are also obtained by homogenizing and precomminuting

| 25 parts by weight | of a compound of the formula I or an active compound mixture of a herbicide and a safener of the formula I, |
|---|---|
| 5 parts by weight | of sodium 2,2'-dinaphthylmethane-6,6'-disulfonate, |
| 2 parts by weight | of sodium oleoyl methyl tauride, |
| 1 parts by weight | of polyvinyl alcohol, |
| 17 parts by weight | of calcium carbonate and |
| 50 parts by weight | of water | on a colloid mill, subsequently grinding the mixture on a bead mill and atomizing and drying the resulting suspension in a spray tower by means of a one-component nozzle.

B. Preparation Examples

1-Isopropylideneaminooxy-2-propyl 5-chloroquinolin-8-oxyacetate (Example 33 in Table 1)

4.75 g (0.02 mol) of 5-chloroquinolin-8-oxyacetate are suspended in 50 ml of tetrahydrofuran, 3.2 g (0.02 mol) of N,N'-carbonyldiimidazole are added and the suspension is heated to 50° C. until the evolution of gas has ended. A solution of 2.62 g (0.02 mol) of 1-isopropylideneaminooxy-2-propanol and 50 mg of sodium in 10 ml of tetrahydrofuran (THF) is added dropwise to this suspension and the mixture is heated under reflux. After the reaction, the THF is stripped off under reduced pressure, the residue is taken up in ethyl acetate and the solution is washed with 5% strength NaOH and NaCl solution. The organic phase is dried over MgSO$_4$ and concentrated and the residue is recrystallized from heptane. 3.6 g (45.6% of theory) of 1-isopropylideneaminooxy-2-propyl 5-chloroquinolin-8-oxyacetate of melting point 102° C. are obtained.

3-(Allyloxy)propyl 5-chloroquinolin-8-oxyacetate (Example 19 in Table 1)

3.78 g (0.021 mol) of 5-chloro-8-hydroxyquinoline and 2.91 g (0.021 mol) of potassium carbonate are heated at 60° C. in 100 ml of dimethylsulfoxide (DMSO) for 30 minutes. The mixture is allowed to cool again to room temperature, 5.0 g (0.021 mol) of 3-(allyloxy)propyl bromoacetate are then added dropwise and the solution is subsequently heated at 90° C. for 4 hours. The DMSO is then distilled off in vacuo, the residue is taken up in ethyl acetate and the solution is washed with water and 5 percent strength sodium hydroxide solution. The organic phase is dried over magnesium sulfate, the desiccant is filtered off and the solvent is stripped off under reduced pressure. After recrystallization of the residue from n-heptane, 5.4 g (76.3% of theory) of 3-(allyloxy)propyl 5-chloroquinolin-8-oxyacetate of melting point 69° C. are obtained.

2-(Propargyloxy)ethyl 5-chloroquinolin-8-oxyacetate (Example 18 in Table 1)

5.0 g (0.021 mol) of 5-chloroquinolin-8-oxyacetic acid are heated at 70° C. in 70 ml of thionyl chloride for one hour. The excess thionyl chloride is then distilled off in vacuo and the residue is suspended in 150 ml of carbon tetrachloride. 2.10 g (0.021 mol) of 2-propargyloxyethanol are added dropwise to this suspension, 2.30 g (0.023 mol) of triethylamine are then added dropwise and the mixture is heated under reflux for 12 hours. The suspension is then washed with in each case 70 ml of 2N HCl and 5 percent strength sodium hydroxide solution, the organic phase is dried over magnesium sulfate and the solvent is stripped off in vacuo. The residue is recrystallized from n-heptane. 1.1 g (16.3% of theory) of 2-(propargyloxy)ethyl 5-chloroquinolin-8-oxyacetate of melting point 53° C. are thus obtained.

2-Allyloxy-1-methylethyl 5-chloroquinolin-8-oxyacetate (Example 24 in Table 1)

5.0 g (0.021 mol) of 5-chloroquinolin-8-oxyacetic acid and 2.44 g (0.021 mol) of 2-allyloxy-1-methylethanol are suspended in a mixture of 40 ml of methylene chloride and 40 ml of dimethylformamide and the suspension is cooled to 0° C. 4.78 g (0.023 mol) of dicyclohexylcarbodiimide, dissolved in 10 ml of methylene chloride, are added dropwise at this temperature, and 200 mg of 3-(N,N-dimethylamino)-pyridine are then added. The mixture is stirred at room temperature for 15 hours and the precipitate which has separated out is filtered off with suction and rinsed with 50 ml of methylene chloride. The filtrate is washed with 100 ml of 0.5 N HCl, with 100 ml of potassium bicarbonate solution and with 3 portions of in each case 50 ml of water. The organic phase is dried over magnesium sulfate and the solvent is stripped off in vacuo. The residue is recrystallized from n-heptane. 5.1 g (72.4% of theory) of 2-allyloxy-1-methylethyl 5-chloroquinolin-8-oxyacetate of melting point 59° C. are obtained in this manner.

The abovementioned preparation examples are listed in the following Tables 1a and 1b with further examples of compounds of the formula I which are prepared in an analogous manner.

TABLE 1

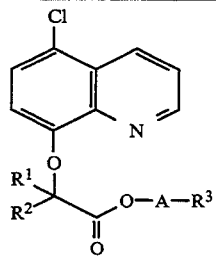

| Example | $R^1$ | $R^2$ | $A-R^3$ | m.p. [°C.] |
|---|---|---|---|---|
| 1 | H | H | $CH_2-Si(CH_3)_3$ | 79 |
| 2 | H | H | $CH_2-CH_2-O-N=C(n.C_4H_9)_2$ | |
| 3 | H | H | $CH(CH_3)-CH_2-O-N=C(C_2H_5)_2$ | 46 |
| 4 | H | H | $CH(C_2H_5)-CH_2-O-N=C(C_2H_5)(n.C_5H_{11})$ | Resin |
| 5 | H | H | $CH_2-C\equiv C-Si(CH_3)_3$ | 122 |
| 6 | $CH_3$ | H | $CH_2-C\equiv C-Si(CH_3)_3$ | 95 |
| 7 | H | H | $CH(CH_3)-C\equiv C-Si(CH_3)_3$ | 72 |
| 8 | $CH_3$ | H | $CH(CH_3)-C\equiv C-Si(CH_3)_3$ | Oil |
| 9 | H | H | $C(CH_3)_2-C\equiv C-Si(CH_3)_3$ | 75 |
| 10 | $CH_3$ | H | $C(CH_3)_2-C\equiv C-Si(CH_3)_3$ | Oil |
| 11 | H | H | $CH_2-CO_2-CH_2-CH=CH_2$ | 85 |
| 12 | H | H | $CH_2-CO_2-CH_2-C\equiv CH$ | |
| 13 | H | H | $CH_2-CO_2-CH_2-Si(CH_3)_3$ | |
| 14 | $CH_3$ | H | $CH_2-CO_2-CH_2-CH=CH_2$ | |
| 15 | $CH_3$ | H | $CH_2-CO_2-CH_2-C\equiv CH$ | |
| 16 | $CH_3$ | H | $CH_2-CO_2-CH_2-Si(CH_3)_3$ | |
| 17 | H | H | $CH_2-CH_2-O-CH_2-CH=CH_2$ | |
| 18 | H | H | $CH_2-CH_2-O-CH_2-C\equiv CH$ | 53 |
| 19 | H | H | $CH_2-CH_2-CH_2-O-CH_2-CH=CH_2$ | 69 |
| 20 | H | H | $CH_2-CH_2-CH_2-O-CH_2-C\equiv CH$ | 73 |
| 21 | H | H | $(CH_2)_4-O-CH_2-CH=CH_2$ | 61 |
| 22 | H | H | $(CH_2)_4-O-CH_2-C\equiv CH$ | |
| 23 | H | H | $(CH_2)_5-O-CH_2-CH=CH_2$ | 63 |

TABLE 1-continued

Structure: 5-chloroquinolin-8-yl ether with -O-CR¹R²-C(=O)-O-A-R³ substituent

| Example | R¹ | R² | A—R³ | m.p. [°C.] |
|---------|----|----|------|------------|
| 24 | H | H | CH(CH₃)—CH₂—O—CH₂—CH=CH₂ | 59 |
| 25 | H | H | CH(CH₃)—CH₂—O—CH₂—C≡CH | |
| 26 | H | H | CH₂—CH₂—O—CH₂—C(CH₃)=CH₂ | 66 |
| 27 | H | H | CH(CH₃)—CH₂—O—CH₂—C(CH₃)=CH₂ | |
| 28 | H | H | CH₂—CH₂—O—CH₂—Si(CH₃)₃ | 56 |
| 29 | H | H | CH₂—CH₂—O—N=C(CH₃)₂ | 93 |
| 30 | H | H | CH₂—CH₂—O—N=C(CH₃)(C₂H₅)... [—N=C with two CH₃ groups via separate bonds] | 58 |
| 31 | H | H | CH₂—CH₂—O—N=cyclopentyl | 79 |
| 32 | H | H | CH₂—CH₂—O—N=cyclohexyl | 83 |
| 33 | H | H | CH(CH₃)—CH₂—O—N=C(CH₃)₂ | 102 |
| 34 | H | H | CH(CH₃)—CH₂—O—N=cyclopentyl | 87 |
| 35 | H | H | CH(CH₃)—CH₂—O—N=cyclohexyl | |
| 36 | H | H | CH(CH₃)—CH₂—O—N=C(CH₃)(C₂H₅ via two CH₃ branches) | Oil |

TABLE 1-continued
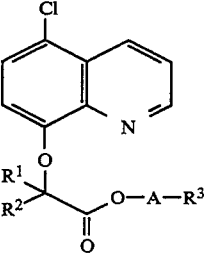
| Example | R¹ | R² | A—R³ | m.p. [°C.] |
|---|---|---|---|---|
| 37 | H | H | CH(CH₃)—CO₂—CH₂—CH=CH₂ | Oil |
| 38 | H | H | CH₂—C(=O)—O—N=C(CH₃)₂ | |
| 39 | H | H | CH₂CH₂—O—CH₂—phenyl | 76 |
| 40 | H | H | CH(CH₃)—CH₂—O—N=cycloheptyl | 64 |
| 41 | H | H | CH₂—CH₂—O—N=cycloheptyl | 87 |
| 42 | H | H | CH(CH₂CH₃)—CH₂—O—N=cycloheptyl | Oil |
| 43 | H | H | CH(CH₂CH₃)—CH₂—O—N=cyclopentyl | |
| 44 | H | H | CH₂—C(=O)—O—N=cyclopentyl | |
| 45 | H | H | CH₂—C(=O)—O—N=cyclohexyl | |
| 46 | H | H | CH₂—C(=O)—O—N=cycloheptyl | |

TABLE 1-continued

[Structure: 5-chloroquinolin-8-yl ether with -O-C(R¹)(R²)-C(=O)-O-A-R³ substituent]

| Example | R¹ | R² | A—R³ | m.p. [°C.] |
|---------|----|----|------|------------|
| 47 | H | H | -CH(CH₃)-C(=O)-O-N=cyclopentyl | |
| 48 | H | H | -CH₂CH₂O-CO-phenyl | 126 |
| 49 | H | H | -CH₂CH₂N=C(CH₃)(CH₃) | |
| 50 | H | H | -CH₂-C(CH₃)=N-O-CH₃ | 90 |
| 51 | H | H | -CH₂-C(=O)-HN-CH₂-CH=CH₂ | |
| 52 | H | H | -CH₂-C(=O)-S-CH₂-CH=CH₂ | |
| 53 | H | H | -CH₂-C(CH₃)=N-n.C₄H₉ | |
| 54 | H | H | -CH₂-C(CH₃)=N-OH | |
| 55 | H | H | -CH₂-C(=O)-N(morpholino) | |
| 56 | H | H | -CH₂-C(=O)-N(2,6-dimethylmorpholino) | |
| 57 | H | H | -CH₂-CH₂-NH-C(=O)-NH-CH₂CH=CH₂ | |
| 58 | H | H | -CH₂-CH₂-O-C(=O)-CH₂-phenyl | |

TABLE 1-continued

[Structure: 5-chloroquinoline with 8-O-C(R¹)(R²)-C(=O)-O-A-R³ substituent]

| Example | R¹ | R² | A—R³ | m.p. [°C.] |
|---|---|---|---|---|
| 59 | H | H | CH₂—C(CH₃)(O—C₂H₅)(O—C₂H₅) [CH₂-C(CH₃) with two O-C₂H₅ groups] | |
| 60 | H | H | CH₂—CH₂—N=C(CH₃)(C₆H₅) | |
| 61 | H | H | CH₂—CH₂—CH₂—O—CH₂Si(CH₃)₃ | |
| 62 | H | H | CH₂—CH₂—CH₂—CH(O—C₂H₅)(O—C₂H₅) | |
| 63 | H | H | CH₂—C(=O)—N(CH₂—CH=CH₂)(CH₂—CH=CH₂) | |
| 64 | H | H | CH(CH₃)—CH(CH₃)—OCH₂CH=CHCH₃ | Wax |
| 65 | CH₃ | H | CH(CH₃)—CH(CH₃)—OCH₂CH=CHCH₃ | Oil |
| 66 | CH₃ | H | CH₂—CH₂—O—CH₂—CH=CH—CH₃ | Oil |
| 67 | CH₃ | H | CH₂—CH₂—O—CH₂—CH=CH₂ | Oil |
| 68 | CH₃ | H | CH(CH₃)—CH(CH₃)—OCH₂CH=CH₂ | Oil |
| 69 | H | H | CH₂—CH(CH₃)—OCH₂CH=CH₂ | 53 |
| 70 | H | H | CH₂—C≡C—CH₂—O—CO—CH₃ | 116 |
| 71 | CH₃ | H | CH₂—CH=CH—CH₂—O—CH₂—CH=CH—CH₃ | Oil |
| 72 | H | H | CH₂—CH=CH—CH₂—O—CH₂—CH=CH—CH₃ | 43 |
| 73 | CH₃ | H | (CH₂)₄—O—CH₂—CH=CH₂ | Oil |
| 74 | H | H | CH(CH₃)—CH(CH₃)—O—CO—CH₃ | Oil |
| 75 | H | H | CH(CH₃)—CH(CH₃)—O—CO-t-C₄H₉ | Oil |
| 76 | H | H | CH₂—CH₂—O—CH₂—CH=CH—CH₃ | 83 |
| 77 | H | H | CH(CH₃)—CH(CH₃)—OCH₂CH=CH₂ | Oil |
| 78 | H | H | CH₂—CH₂—N=cyclohexylidene | 155 |
| 79 | H | H | CH(C₂H₅)—CH₂—OCH₂C≡CH | Oil |
| 80 | H | H | CH₂—CH₂—O—CO-t-C₄H₉ | 38 |
| 81 | H | H | CH₂—CH₂—O—N=C(CH₃)C₂H₅ | 68 |
| 82 | H | H | CH(C₂H₅)—CH₂—OCH₂CH=CH₂ | Oil |
| 83 | H | H | CH(C₂H₅)—CH₂—O—N=C(CH₃)₂ | Oil |
| 84 | H | H | CH₂—CH₂—O—CO—CH₃ | 87 |
| 85 | H | H | CH₂—CH=CH—CH₂—O—CO—CH₃ | 73 |
| 86 | H | H | CH₂—CH₂—NH—CO—CF₃ | 117 |
| 87 | H | H | CH₂—CH=CH—CH₂—O—CH₂—CH=CH₂ | 47 |
| 88 | H | H | CH(CH₃)—CH₂—O—N=C(C₂H₅)n-C₅H₁₁ | Resin |
| 89 | H | H | CH₂—CH₂—CH₂—NH—CO—CH₃ | 133 |
| 90 | H | H | CH₂—CH₂—CH₂—NH—CO—CH₂—CH₃ | 105 |
| 91 | H | H | CH₂—CH₂—NH—CO—CH₂—CH₃ | 119 |
| 92 | H | H | CH₂—CH₂—O—N=C(n-C₄H₉)—C₂H₅ | |
| 93 | H | H | CH₂—CH₂—O—CH₂—CH=C(CH₃)₂ | 67 |

TABLE 1-continued

[Structure: 5-chloroquinoline with 8-O-C(R¹)(R²)-C(=O)-O-A-R³ substituent]

| Example | R¹ | R² | A—R³ | m.p. [°C.] |
|---|---|---|---|---|
| 94 | H | H | CH₂—CH₂—O—CH₂—CH(—O—)C(CH₃)(CH₃)(—O—CH—) (dioxolane with CH₃,CH₃) | 38 |
| 95 | CH₃ | H | CH(CH₃)—CH₂—OCH₂—CH=CH₂ | Oil |
| 96 | H | H | CH₂—CH₂—CH₂—C(CH₃)=N—OH | 84 |
| 97 | H | H | CH₂—C(CH₃)₂—CH₂—NH—CO—C₆H₅ | Oil |
| 98 | H | H | CH₂—CH₂—NH—CO—C₆H₅ | 122 |
| 99 | H | H | CH₂—CH₂—CH₂—C(CH₃)=N—O—CO—CH₃ | 85 |
| 100 | H | H | CH(CH₃)—CH(CH₃)—O—CO—CH₂—O—CH₃ | 92 |
| 101 | H | H | (CH₂)₂OCH₂CH=C(CH₃)CH₂CH₂CH=C(CH₃)₂ | 39 |
| 102 | H | H | CH₂—CH=CH—CH₂—O—CO—CH₃ | 75 |
| 103 | H | H | CH₂—CH₂—CH₂—NH—CO—C₆H₅ | |
| 104 | H | H | CH₂—CH₂—O—CO—CH₂—CH₃ | 55 |
| 105 | H | CH₃ | CH₂—CO—O—CH₂—CH=CH₂ | Oil |
| 106 | CH₃ | H | CH₂—CH=CH—CH₂—O—CH₂—CH=CH₂ | |
| 107 | CH₃ | CH₃ | CH₂—CH=CH—CH₂—O—CH₂—CH=CH₂ | |
| 108 | CH₃ | H | CH₂—CH₂—NH—CO—CF₃ | |
| 109 | CH₃ | H | CH₂—CH=CH—CH₂—O—CO—CH₃ | |
| 110 | CH₃ | H | CH₂—CH₂—O—CO—CH₃ | |
| 111 | CH₃ | H | CH(C₂H₅)—CH₂—O—N=C(CH₃)₂ | |
| 112 | CH₃ | H | CH(C₂H₅)—CH₂—O—CH₂—CH=CH₂ | |
| 113 | CH₃ | H | CH₂—CH₂—O—N=C(CH₃)C₂H₅ | |
| 114 | CH₃ | H | CH₂—CH₂—O—CO-t-C₄H₉ | |
| 115 | CH₃ | H | CH(C₂H₅)—CH₂—O—CH₂—C≡CH | |
| 116 | CH₃ | H | CH₂—CH₂—N=cyclohexylidene | |
| 117 | CH₃ | H | CH(CH₃)—CH(CH₃)—O—CH₂—CH=CH₂ | |
| 118 | CH₃ | H | CH₂—CH₂—O—CH₂—CH=CH—CH₃ | |
| 119 | CH₃ | H | CH₂—CH₂—O—CO—CH₂—O—CH₃ | |
| 120 | CH₃ | H | CH₂—CH₂—CH₂—C(CH₃)=N—O—CO—CH₃ | |
| 121 | CH₃ | H | CH₂—CH₂—NH—CO—C₆H₅ | |
| 122 | CH₃ | H | CH₂—C(CH₃)₂—CH₂—NH—CO—C₆H₅ | |
| 123 | CH₃ | H | CH₂—CH₂—CH₂—C(CH₃)=N—OH | |
| 124 | H | H | CH₂—CH₂—CH₂—NH—CO—CH=CH₂ | |
| 125 | H | H | CH₂—CH₂—CH₂—NH—CO—C≡CH | |
| 126 | CH₃ | H | CH₂—CH₂—CH₂—NH—CO—CH=CH₂ | |
| 127 | CH₃ | H | CH₂—CH₂—CH₂—NH—CO—C≡CH | |
| 128 | H | H | CH₂—CH=CH—CH₂—NH—CO—CH₃ | |

TABLE 1-continued

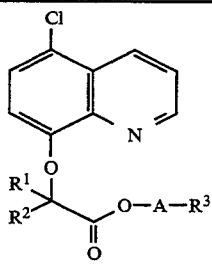

| Example | R¹ | R² | A—R³ | m.p. [°C.] |
|---|---|---|---|---|
| 129 | H | H | 2-methylcyclohexyl-O-CH₂-CH=CH₂ | |
| 130 | H | H | 2-methylcyclohexyl-O-CH₂-C≡CH | |
| 131 | CH₃ | H | 2-methylcyclohexyl-O-CH₂-CH=CH₂ | |
| 132 | CH₃ | H | 2-methylcyclohexyl-O-CH₂-C≡CH | |
| 133 | H | H | 2-methylcyclohexyl-O-N=C(CH₃)₂ | |
| 134 | H | H | CH₂—CH₂—O—CH₂-p-C₆H₄—Br | |
| 135 | H | H | CH₂—CH₂—CH₂—O—CH₂-p-C₆H₄—NO₂ | |
| 136 | H | H | CH(CH₃)—CH₂—O—CH₂-m-C₆H₄—CH₃ | |
| 137 | H | H | CH₂—CH(CH₃)—O—CH₂-p-C₆H₄—CF₃ | |
| 138 | H | H | CH₂—CH₂—O—CH₂-p-C₆H₄—O—CHF₂ | |
| 139 | H | H | CH₂—CH₂—O—CO—CH₂—C₆H₅ | |
| 140 | H | H | CH₂—CH₂—C(CH₃)(O—CH₂—CH₃)(O—CH₂—CH₃) | |
| 141 | H | H | CH₂—CH₂—C(CH₃)(1,3-dioxolane) | |
| 142 | H | H | CH₂—CH₂—CH₂—O—CO—CH₂—Cl | |
| 143 | H | H | CH₂—CH₂—NH—CO-2,4-Cl₂C₆H₃ | |
| 144 | H | H | CH₂—C(CH₃)₂—CH₂—NH—CO—CH₂—C₆H₅ | |
| 145 | H | H | CH₂—CH₂—CO—N(CH₃)₂ | |
| 146 | H | H | CH₂—CO—NH—CH₂—CH=CH₂ | |
| 147 | H | H | CH(CH₃)—CO—NH-n-C₄H₉ | |
| 148 | H | H | CH₂—CH₂—CH₂—CO—NH—CH₂—C≡CH | |
| 149 | H | H | CH₂—CH₂—CH₂—C(=S)—CH₃ | |
| 150 | H | H | CH(CH₃)—CH₂—CH₂—S—CH₂—CH=CH₂ | |
| 151 | H | H | CH₂—CH=CH—CH₂—CO—N(CH₃)₂ | |
| 152 | H | H | CH₂—CH=CH—CH₂—S—CH₂—CH=CH₂ | |

TABLE 1-continued

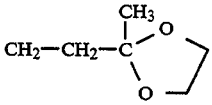

| Example | R¹ | R² | A—R³ | m.p. [°C.] |
|---|---|---|---|---|
| 153 | H | H | CH₂—CH=CH—CH₂—O—CO—CH₂—Cl | |
| 154 | H | H | CH₂—CH=CH—CH₂—O—CO—CH₂—C₆H₅ | |
| 155 | H | H | CH₂—CH=CH—CH₂—NH—CO—CH₂—C₆H₅ | |
| 156 | H | H | CH₂—CH=CH—CH₂—CO—NH—CH₂—CH=CH₂ | |
| 157 | H | H | CH₂—CH=CH—CH₂—O—CH₂-p-C₆H₄—OCHF₂ | |
| 158 | H | H | CH₂—CH=CH—CH₂—O—N=C(CH₃)₂ | |
| 159 | H | H | CH₂—CH=CH—CH₂—O—CH₂—C≡CH | |
| 160 | H | H | CH₂—CH=CH—CH₂—O—CH₂—C(CH₃)=CH₂ | |
| 161 | H | H | CH₂—C≡C—CH₂—O—CO—C₆H₅ | |
| 162 | H | H | CH₂—C≡C—CH₂—NH—CO—CH₃ | |
| 163 | H | H | CH₂—C≡C—CH₂—NH—CO—CH₂—OCH₃ | |
| 164 | H | H | CH₂—C≡C—CH₂—O—N=C(CH₃)₂ | |
| 165 | H | H | CH₂—C≡C—CH₂—O—CH₂—C≡CH | |
| 166 | H | H | CH₂—C≡C—CH₂—N—CO—CH₂—C₆H₅ | |
| 167 | H | H | CH₂—C≡C—CH₂—CS—CH₃ | |
| 168 | H | CH₃ | CH₂—CH₂—O—CH₂-p-C₆H₄Br | |
| 169 | H | CH₃ | CH₂CH₂CH₂—O—CH₂-p-C₆H₄NO₂ | |
| 170 | H | CH₃ | CH(CH₃)—CH₂—CH₂—O—CH₂-m-C₆H₄—CH₃ | |
| 171 | H | CH₃ | CH₂—CH(CH₃)—O—CH₂-p-C₆H₄—CF₃ | |
| 172 | H | CH₃ | CH₂—CH₂—CO—O—CH₂—C₆H₅ | |
| 173 | H | CH₃ | CH₂—CH₂—C(OCH₂—CH₃)₂(CH₃) | |
| 174 | H | CH₃ | CH₂—CH₂—C(CH₃)(O—CH₂—CH₂—O) (cyclic) | |
| 175 | H | CH₃ | CH₂—CH₂—CH₂—O—CO—CH₂—Cl | |
| 176 | H | CH₃ | CH₂—CH₂—NH—CO-2,4-Cl₂C₆H₃ | |
| 177 | H | CH₃ | CH₂—C(CH₃)₂—CH₂—NH—CO—CH₂—C₆H₅ | |
| 178 | H | CH₃ | CH₂—CH₂—CO—N(CH₃)₂ | |
| 179 | H | CH₃ | CH₂—CO—NH—CH₂—CH=CH₂ | |
| 180 | H | CH₃ | CH(CH₃)—CO—NH-n-C₄H₉ | |
| 181 | CH₃ | H | CH₂—CH₂—CH₂—CO—NH—CH₂—C≡CH | |
| 182 | H | CH₃ | CH₂—CH₂—CH₂—CS—CH₃ | |
| 183 | H | CH₃ | CH(CH₃)—CH₂—CH₂—S—CH₂—CH=CH₂ | |
| 184 | H | CH₃ | CH₂—CH=CH—CH₂—CO—N(CH₃)₂ | |
| 185 | H | CH₃ | CH₂—CH=CH—CH₂—S—CH₂—CH=CH₂ | |
| 186 | H | CH₃ | CH₂—CH=CH—CH₂—O—CO—CH₂—Cl | |
| 187 | H | CH₃ | CH₂—CH=CH—CH₂—NH—CO—CH₂—C₆H₅ | |
| 188 | H | CH₃ | CH₂—CH=CH—CH₂—O—N=C(CH₃)₂ | |
| 189 | H | CH₃ | CH₂—CH=CH—CH₂—O—CH₂—C≡CH | |
| 190 | H | CH₃ | CH₂—CH=CH—CH₂—O—CH₂—C(CH₃)=CH₂ | |
| 191 | H | CH₃ | CH₂—C≡C—CH₂—O—N=C(CH₃)₂ | |
| 192 | H | CH₃ | CH₂—C≡C—CH₂—NH—CO—CH₃ | |
| 193 | H | CH₃ | CH₂—C≡C—CH₂—NH—CO—CH₂—O—CH₃ | |
| 194 | H | CH₃ | CH₂—C≡C—CH₂—O—CH₂—C≡CH | |
| 195 | H | CH₃ | CH₂—C≡C—CH₂—NH—CO—CH₂—C₆H₅ | |
| 196 | H | CH₃ | CH₂—C≡C—CH₂—O—CO—CH₃ | |
| 197 | H | H | CH₂—CH₂—CH₂—O—CO-t-C₄H₉ | 82 |
| 198 | H | H | CH₂—CH₂—CH₂—O—CO—CH₂—CH₃ | 76 |
| 199 | H | H | CH₂—CH₂—CH₂—O—CO—CH₃ | 113 |
| 200 | H | H | CH₂—CH₂—O—CO—CO—CH₂—CH(CH₃)₂ | 61 |
| 201 | H | H | CH₂—CH₂—O—CO—CH₂—Cl | 90 |
| 202 | H | H | CH₂—CH₂—O—CO—CF₃ | 103 |
| 203 | H | H | CH₂—CH₂—O—CO-cyclo-C₃H₅ | 72 |

TABLE 1b

[Structure: 5-chloroquinoline with 8-O-C(R¹)(R²)-C(=O)-N(H)-A-R³ substituent]

| Example | R¹ | R² | A—R³ | m.p. [°C.] |
|---|---|---|---|---|
| 204 | H | H | CH₂—CH₂—O—CO—CH₃ | 106 |
| 205 | H | H | CH₂—CH₂—O—CO-t-C₄H₉ | 96 |
| 206 | H | H | CH₂—CH₂—CH₂—O—CO—CH=C(CH₃)₂ | Oil |
| 207 | H | H | CH₂—CH₂—NH—CO—C₂H₅ | 164 |
| 208 | H | H | CH₂—CH₂—CH₂—NH—CO—CH₃ | 81 |
| 209 | H | H | CH(CH₃)—CH₂—O—CH₂—CH=CH₂ | |
| 210 | H | H | CH₂—CH₂—O—N=C(CH₃)₂ | |
| 211 | H | H | CH₂—CO—O—CH₂—CH=CH₂ | |
| 212 | H | H | CH₂—CO—O—CH₂—C≡CH | |
| 213 | H | H | CH₂—CH(CH₃)—O—CH₂—CH=CH₂ | |
| 214 | H | H | CH₂—CH₂—CH₂—CH₂—O—CH₂—CH=CH₂ | |
| 215 | H | H | CH₂—CH₂—O—CH₂—CH=CH₂ | |
| 216 | H | H | CH₂—CH₂—CH₂—O—CH₂—CH=CH₂ | |
| 217 | H | H | CH₂—CH₂—O—CH₂—C≡CH | |
| 218 | H | H | CH₂—CH₂—CH₂—O—CH₂—C≡CH | |
| 219 | H | H | CH₂—CH₂—CH₂—CH₂—O—CH₂—C≡CH | |
| 220 | H | H | CH₂—CH₂—CO—NH—CH₂—C₆H₅ | |
| 221 | H | H | CH₂—CH=CH—CH₂—O—CH₂—CH=CH₂ | |
| 222 | H | H | CH₂—CH=CH—CH₂—O—CH₂—C≡CH | |
| 223 | H | H | CH₂—CH=CH—CH₂—O—CH₂—C₆H₅ | |
| 224 | H | H | CH₂—CH₂—O—CO—CH₂—C₆H₅ | |
| 225 | H | H | CH₂—CH₂—N=cyclohexyl | |
| 226 | H | H | CH₂—CH₂—(2-methylcyclohexyl)—O—CH₂—CH=CH₂ | |
| 227 | H | H | CH₂—CH₂—(2-methylcyclohexyl)—O—CH₂—C≡CH | |
| 228 | H | H | CH₂—CH₂—C(OC₂H₅)(OC₂H₅)(CH₃) | |
| 229 | H | H | CH₂—CH₂—C(CH₃)(1,3-dioxolan-2-yl) | |
| 230 | H | H | CH₂—CH₂—NH—CO—C≡CH | |
| 231 | H | H | CH₂—CH₂—O—CH-p-C₆H₄—NO₂ | |
| 232 | H | H | CH₂—CH₂—O—CO—CH₂—O—CH₃ | |
| 233 | H | H | CH₂—CH₂—CO—N(CH₃)₂ | |
| 234 | H | H | CH(CH₃)—CO—NH—C₄H₉ | |
| 235 | H | H | CH₂—CH=CH—CH₂—CO—N(CH₃)₂ | |
| 236 | H | H | CH₂—C≡C—CH₂—CO—NH—CH₂—C₆H₅ | |
| 237 | H | CH₃ | CH₂—CH₂—CH₂—NH—CO—CH₃ | |
| 238 | H | CH₃ | CH₂—CH₂—O—N=C(CH₃)₂ | |
| 239 | H | CH₃ | CH₂—CH₂—O—CH₂—C≡CH | |
| 240 | H | CH₃ | CH(CH₃)—CH₂—O—CH₂—CH=CH₂ | |
| 241 | H | CH₃ | CH₂—CO—O—CH₂—CH=CH₂ | |

TABLE 1b-continued

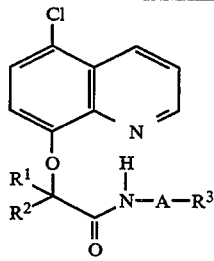

| Example | R¹ | R² | A—R³ | m.p. [°C.] |
|---|---|---|---|---|
| 242 | H | CH₃ | CH₂—CH₂—CH₂—CH₂—O—CH₂—CH=CH₂ | |
| 243 | H | CH₃ | CH₂—CH(CH₃)—O—CH₂—CH=CH₂ | |
| 244 | H | CH₃ | CH₂—CH=CH—CH₂—O—CH₂—CH=CH₂ | |
| 245 | H | CH₃ | CH₂—CH=CH—CH₂—O—CO—CH₃ | |
| 246 | H | CH₃ | CH₂—CH=CH—CH₂—NH—CO—C₆H₅ | |
| 247 | H | CH₃ | CH₂—CH₂—N=⟨cyclohexyl⟩ | |
| 248 | H | CH₃ | CH₂—CH₂—CH₂—C(CH₃)=N—O—CO—CH₃ | |
| 249 | H | CH₃ | CH₂—CH₂—CH₂—C(CH₃)=N—OH | |
| 250 | H | CH₃ | CH₂—CH₂—NH—CO—C≡CH | |
| 251 | H | CH₃ | CH₂—C(CH₃)₂—CH₂—NH—CO—CH₂—C₆H₅ | |
| 252 | H | CH₃ | CH₂—CH₂—NH—CO—CF₃ | |
| 253 | H | CH₃ | CH₂—CH₂—O—CH₂—Si(CH₃)₃ | |
| 254 | H | CH₃ | CH₂—C≡C—CH₂—O—CH₂—CH=CH₂ | |
| 255 | H | CH₃ | CH₂—C≡C—CH₂—NH—CO—CH₃ | |
| 256 | H | CH₃ | CH₂—C≡C—CH₂—O—CH₂—C₆H₅ | |
| 257 | H | CH₃ | CH₂—C≡C—CH₂—CS—CH₃ | |
| 258 | H | CH₃ | CH₂—C≡C—CH₂—O—N=C(CH₃)₂ | |
| 259 | CH₃ | CH₃ | CH₂—CH₂—O—CH₂—C≡CH | |
| 260 | CH₃ | CH₃ | CH₂—CH₂—CH₂—CH₂—O—CH₂—CH=CH₂ | |
| 261 | CH₃ | CH₃ | CH₂—CH₂—O—CH₂—Si(CH₃)₃ | |
| 262 | CH₃ | CH₃ | CH(CH₃)—CH₂—O—CH₂—CH=CH₂ | |
| 263 | CH₃ | CH₃ | CH₂—CH₂—O—N=C(CH₃)₂ | |
| 264 | CH₃ | CH₃ | CH₂—CO—O—CH₂—CH=CH₂ | |
| 265 | CH₃ | CH₃ | CH₂—CO—NH—CH₂—C≡CH | |
| 266 | H | H | CH₂CH₂CH₂—O—CO—CH₂—O—CH₃ | Oil |
| 267 | H | H | CH₂CH₂CH₂—O—CO—CH₂—O—C₂H₅ | 81 |
| 268 | H | H | CH₂CH₂—NH—CO—NH—C₆H₅ | 158 |

C. BIOLOGICAL EXAMPLES

Example 1

Wheat and barley were grown to the 3–4 leaf stage in plastic pots in a greenhouse and then treated successively, by the post-emergence method, with the compounds according to the invention and the herbicides tested. The herbicides and the compounds of the formula I were applied here in the form of aqueous suspensions or emulsions with an amount of water applied of, when converted, 300 l/ha. 3–4 weeks after the treatment, the plants were rated visually for any type of damage due to the herbicides applied, the extent of persistent inhibition of growth being taken into account in particular. The results were evaluated in percentage values in comparison with untreated controls.

The results from Table 2 illustrate that the compounds according to the invention can effectively reduce severe herbicidal damage to crop plants.

Even at high overdoses of the herbicide, severe damage which occurred to the crop plants was significantly reduced, and milder damage was eliminated completely. Mixtures of herbicides and compounds according to the invention are therefore eminently suitable for selective combating of weeds in cereal crops.

| Plant species | Growth stage | Growth height (cm) |
|---|---|---|
| TRAE *Triticum aestivum* (summer) | 13–21 | 23–25 |
| HOVU *Hordeum vulgare* (summer) | 13–21 | 30–32 |
| TRDU *Triticum durum* | 21–22 | 18–20 |
| ALMY *Alopecurus myosuroides* | 21–22 | 12–14 |

TABLE 2

| Active compound(s) | Dose kg of Active Compound/ha | % damage to | | | |
|---|---|---|---|---|---|
| | | TRAE | HOVU | TRDU | ALMY |
| H | 0.8 | 0 | 100 | 93 | — |
| | 0.4 | 0 | 100 | 50 | — |
| | 0.2 | 0 | 100 | 40 | — |
| | 0.1 | 0 | 99 | 20 | 70 |
| | 0.05 | — | — | — | 10 |

TABLE 2-continued

| Active compound(s) | Dose kg of Active Compound/ha | % damage to TRAE | HOVU | TRDU | ALMY |
|---|---|---|---|---|---|
| | 0.025 | — | — | — | 0 |
| H + 39 | 0.8 + 0.2 | 0 | 10 | 0 | — |
| | 0.4 + 0.1 | 0 | 10 | 0 | — |
| | 0.2 + 0.05 | 0 | 10 | 0 | — |
| | 0.1 + 0.025 | 0 | 10 | 0 | 95 |
| | 0.5 + 0.012 | — | — | — | 93 |
| | 0.025 + 0.006 | — | — | — | 85 |
| H + 19 | 0.8 + 0.2 | 0 | 0 | 0 | — |
| | 0.4 + 0.1 | 0 | 0 | 0 | — |
| | 0.2 + 0.05 | 0 | 0 | 0 | — |
| | 0.1 + 0.025 | 0 | 0 | 0 | 97 |
| | 0.05 + 0.012 | — | — | — | 85 |
| | 0.025 + 0.006 | — | — | — | 30 |
| H + 11 | 0.8 + 0.2 | 0 | 0 | 0 | — |
| | 0.4 + 0.05 | 0 | 0 | 0 | — |
| | 0.2 + 0.05 | 0 | 0 | 0 | — |
| | 0.1 + 0.025 | 0 | 0 | 0 | 95 |
| | 0.05 + 0.012 | — | — | — | 95 |
| | 0.025 + 0.006 | — | — | — | 60 |
| H + 20 | 0.8 + 0.2 | 0 | 0 | 0 | — |
| | 0.4 + 0.1 | 0 | 0 | 0 | — |
| | 0.2 + 0.05 | 0 | 0 | 0 | — |
| | 0.1 + 0.025 | 0 | 0 | 0 | 95 |
| | 0.05 + 0.012 | — | — | — | 93 |
| | 0.025 + 0.006 | — | — | — | 70 |
| H + 28 | 0.8 + 0.2 | 0 | 10 | 35 | — |
| | 0.4 + 0.1 | 0 | 10 | 40 | — |
| | 0.2 + 0.05 | 0 | 0 | 10 | — |
| | 0.1 + 0.025 | 0 | 0 | 0 | 85 |
| | 0.05 + 0.012 | — | — | — | 85 |
| | 0.025 + 0.006 | — | — | — | 70 |
| H + 24 | 0.8 + 0.2 | 0 | 0 | 0 | — |
| | 0.4 + 0.1 | 0 | 0 | 0 | — |
| | 0.2 + 0.05 | 0 | 0 | 0 | — |
| | 0.1 + 0.025 | 0 | 0 | 0 | 99 |
| | 0.05 + 0.012 | — | — | — | 95 |
| | 0.025 + 0.006 | — | — | — | 80 |
| H + 23 | 0.8 + 0.2 | 0 | 0 | 0 | — |
| | 0.4 + 0.1 | 0 | 0 | 0 | — |
| | 0.2 + 0.05 | 0 | 0 | 0 | — |
| | 0.1 + 0.025 | 0 | 0 | 0 | 93 |
| | 0.05 + 0.012 | — | — | — | 93 |
| | 0.025 + 0.006 | — | — | — | 55 |
| H + 21 | 0.8 + 0.2 | 0 | 0 | 0 | — |
| | 0.4 + 0.1 | 0 | 0 | 0 | — |
| | 0.2 + 0.05 | 0 | 0 | 0 | — |
| | 0.1 + 0.025 | 0 | 0 | 0 | 95 |
| | 0.05 + 0.012 | — | — | — | 93 |
| | 0.025 + 0.006 | — | — | — | 45 |
| H + 29 | 0.8 + 0.2 | 0 | 0 | 0 | — |
| | 0.4 + 0.1 | 0 | 0 | 0 | — |
| | 0.2 + 0.05 | 0 | 0 | 0 | — |
| | 0.1 + 0.025 | 0 | 0 | 0 | 98 |
| | 0.05 + 0.012 | — | — | — | 90 |
| | 0.025 + 0.006 | — | — | — | 90 |
| H + 18 | 0.8 + 0.2 | 0 | 10 | 0 | — |
| | 0.4 + 0.1 | 0 | 0 | 0 | — |
| | 0.2 + 0.05 | 0 | 0 | 0 | — |
| | 0.1 + 0.025 | 0 | 0 | 0 | 98 |
| | 0.05 + 0.012 | — | — | — | 90 |
| | 0.025 + 0.006 | — | — | — | 60 |
| H + 22 | 0.8 + 0.2 | 0 | 5 | 5 | — |
| | 0.4 + 0.1 | 0 | 0 | 0 | — |
| | 0.2 + 0.05 | 0 | 0 | 0 | — |
| | 0.1 + 0.025 | 0 | 0 | 0 | — |
| H + 98 | 0.8 + 0.2 | 0 | 10 | 0 | — |
| | 0.4 + 0.1 | 0 | 0 | 0 | — |
| | 0.2 + 0.05 | 0 | 0 | 0 | — |
| | 0.1 + 0.025 | 0 | 0 | 0 | — |
| H + 99 | 0.8 + 0.2 | 0 | 10 | 10 | — |
| | 0.4 + 0.1 | 0 | 0 | 0 | — |
| | 0.2 + 0.05 | 0 | 0 | 0 | — |
| H + 100 | 0.8 + 0.2 | 0 | 0 | 5 | — |
| | 0.4 + 0.1 | 0 | 0 | 0 | — |
| | 0.2 + 0.05 | 0 | 0 | 0 | — |
| H + 96 | 0.8 + 0.2 | 0 | 10 | 5 | — |
| | 0.4 + 0.1 | 0 | 0 | 0 | — |
| | 0.2 + 0.05 | 0 | 0 | 0 | — |
| H + 201 | 0.8 + 0.2 | 0 | 10 | 15 | — |
| | 0.4 + 0.1 | 0 | 10 | 5 | — |
| | 0.2 + 0.05 | 0 | 0 | 0 | — |
| H + Comparison example from EP 191 736 | 0.8 + 0.2 | 0 | 0 | 35 | — |
| | 0.4 + 0.1 | 0 | 0 | 10 | — |
| | 0.2 + 0.05 | 0 | 0 | 0 | — |
| | 0.1 + 0.025 | 0 | 0 | 0 | 95 |
| | 0.05 + 0.012 | — | — | — | 90 |
| | 0.025 + 0.006 | — | — | — | 25 |
| H + Comparison example from EP 94 349 | 0.8 + 0.2 | 0 | 0 | 5 | — |
| | 0.4 + 0.1 | 0 | 0 | 5 | — |
| | 0.2 + 0.05 | 0 | 0 | 0 | — |
| | 0.1 + 0.025 | 0 | 0 | 0 | 95 |
| | 0.05 + 0.012 | — | — | — | 95 |
| | 0.024 + 0.006 | — | — | — | 35 |

Abbreviations in Table 2:
—=not tested
H=ethyl 2-(4-(6-chlorobenzoxazol-2-yl-oxy)-phenoxy)-propionate (number)=antidote with same number from Tables 1a and 1b
Comparison example from EP-191 736 corresponds to formula I, in which $R^1=R^2=H$ and $X-A-R^3$ is replaced by 2-phenoxyethoxy
Comparison example from EP-94 349 corresponds to formula I, in which $R^1=R_2=H$ and $2X-A-R^3$ is replaced by ethoxy.

Example 2

The maize plants, broad-leaved weeds and gramineous weeds were grown to the 4- to 5-leaf stage in the open or in the greenhouse in plastic pots and treated successively, by the post-emergence method, with herbicides and compounds of the formula I according to the invention. The active compounds were applied here in the form of aqueous suspensions or emulsions with an amount of water applied of, when converted, 300 l/ha. 4 weeks after the treatment, the plants were rated visually for any type of damage by the herbicides applied, the extent of persistent inhibition of growth being taken into account in particular. The results were evaluated in percentage values in comparison with untreated controls.

The results show (see, for example, Table 3) that the compounds of the formula I according to the invention which are employed can effectively reduce severe herbicide damage to the maize plants. Even at high overdoses of the herbicides, severe damage which occurs to the crop plants is significantly reduced, and milder damage is eliminated completely. Mixtures of herbicides and compounds of the formula I are therefore eminently suitable for selectively combating weeds in maize.

TABLE 3

| Active compound(s) | Dose kg of Active Compound/ha | % damage to maize |
|---|---|---|
| SH1 | 50 | 90 |
| | 25 | 75 |
| | 12 | 35 |
| SH1 + 1 | 50 + 50 | 10 |
| | 25 + 25 | 0 |
| | 12 + 12 | 0 |
| SH1 + 11 | 50 + 50 | 5 |
| | 25 + 25 | 0 |
| | 12 + 12 | 0 |
| SH1 + 21 | 50 + 50 | 10 |
| | 25 + 25 | 0 |
| | 12 + 12 | 0 |

TABLE 3-continued

| Active compound(s) | Dose kg of Active Compound/ha | % damage to maize |
|---|---|---|
| SH1 + 24 | 50 + 50 | 5 |
|  | 25 + 25 | 0 |
|  | 12 + 12 | 0 |
| SH1 + 17 | 50 + 50 | 0 |
|  | 25 + 25 | 0 |
|  | 12 + 12 | 0 |
| SH1 + 50 | 50 + 50 | 10 |
|  | 25 + 25 | 0 |
|  | 12 + 12 | 0 |
| SH1 + 70 | 50 + 50 | 10 |
|  | 25 + 25 | 0 |
|  | 12 + 12 | 0 |
| SH1 + 84 | 50 + 50 | 5 |
|  | 25 + 25 | 0 |
| SH1 + 86 | 50 + 50 | 15 |
|  | 25 + 25 | 0 |
| SH1 + 87 | 50 + 50 | 20 |
|  | 25 + 25 | 0 |
| SH1 + 95 | 50 + 50 | 15 |
|  | 25 + 25 | 0 |
| SH1 + 96 | 50 + 50 | 5 |
|  | 25 + 25 | 0 |
| SH1 + 98 | 50 + 50 | 5 |
|  | 25 + 25 | 0 |
| SH1 + 99 | 50 + 50 | 10 |
|  | 25 + 25 | 0 |
| SH1 + 100 | 50 + 50 | 10 |
|  | 25 + 25 | 0 |
| SH1 + 201 | 50 + 50 | 15 |
|  | 25 + 25 | 0 |
| SH1 + 204 | 50 + 50 | 5 |
|  | 25 + 25 | 0 |
| SH1 + 207 | 50 + 50 | 15 |
|  | 25 + 25 | 0 |
| IM1 | 200 | 60 |
|  | 100 | 30 |
|  | 50 | 20 |
| IM1 + 24 | 200 + 200 | 5 |
|  | 100 + 100 | 0 |
|  | 50 + 50 | 0 |
| IM1 + 96 | 200 + 200 | 5 |
|  | 100 + 100 | 0 |
|  | 50 + 50 | 0 |
| IM1 + 95 | 200 + 200 | 10 |
|  | 100 + 100 | 0 |
|  | 50 + 50 | 0 |
| IM2 | 100 | 40 |
|  | 50 | 25 |
| IM2 + 21 | 100 + 100 | 0 |
|  | 50 + 50 | 0 |
| IM2 + 24 | 100 + 100 | 0 |
|  | 50 + 50 | 0 |
| IM2 + 96 | 100 + 100 | 10 |
|  | 50 + 50 | 0 |

Abbreviations in Table 3:

SH1 = 3-(4,6-dimethoxypyrimidin-2-yl)-1-[3-(N-methyl-N-methylsulfonyl-amino)-2-pyridyl-sulfonyl]-urea IM1 = ammonium 5-ethyl-2-(4-isopropyl-4-methyl-5-oxo-2-imidazolin-2-yl)-pyridine-3-carboxylate (imazethapyr ammonium)

IM2 = rac-2-[4,5-dihydro-4-methyl-4-(1-methylethyl)-5-oxo-1H-imidazol-2-yl]-5-methyl-3-pyridinecarboxylic acid (imazethamethapyr)

(number) = antidote with same number from Tables 1a or 1b

We claim:

1. A compound of the formula (I),

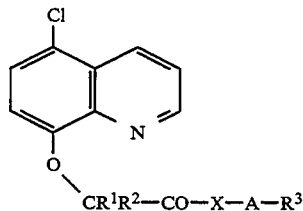

in which $R^1$ and $R^2$ independently of one another are H or $(C_1-C_4)$-alkyl, X is O or S, A is $(C_1-C_4)$-alkylene, $(C_4-C_6)$-alkenylene, $(C_4-C_6)$-alkynylene, or $(C_3-C_8)$-cycloalkylene, $R^3$ is $(C_3-C_6)$-alkenyloxy, $(C_3-C_6)$-alkynyloxy, phenyl-$(C_1-C_4)$-alkoxy, in which the phenyl ring is unsubstituted or substituted by one or more radicals selected from the group consisting of halogen, nitro, $(C_1-C_4)$-alkyl, $(C_1-C_4)$-alkoxy, $(C_1-C_4)$-haloalkyl and $(C_1-C_4)$ haloalkoxy; or, is $(C_3-C_6)$-alkenyloxycarbonyl, $(C_3-C_6)$alkynyloxycarbonyl, phenyl-$(C_1-C_4)$-alkoxycarbonyl, in which the phenyl ring is unsubstituted or substituted by one or more radicals selected from the group consisting of halogen, nitro, $(C_1-C_4)$-alkyl, $(C_1-C_4)$alkoxy, $(C_1-C_4)$-haloalkyl and $(C_1-C_4)$-haloalkoxy; or, is $(C_2-C_6)$-alkenylcarbonyl, $(C_2-C_6)$-alkynylcarbonyl, a radical of the formula $R^8O—CH(OR^9)—$ or $R^8O—CH(OR^9)—(CH_2)_n—O—$, in which n is 0, or 2; or, is an alkoxy radical of the formula $R^8O—CHR^{10}—CH(OR^9)-(C_1-C_4)$-alkoxy; or, is $(C_1-C_6)$-alkylcarbonyloxy in which the alkyl is unsubstituted or substituted by one or more radicals selected from the group consisting of halogen, nitro, $(C_1-C_4)$-alkoxy, phenyl and phenyl substituted by one or more of halogen, nitro, $(C_1-C_4)$-alkyl, $(C_1-C_4)$-alkoxy, $(C_1-C_4)$-haloalkyl or $(C_1-C_4)$-haloalkoxy; or, is $(C_1-C_6)$-alkenylcarbonyloxy, $(C_2-C_6)$-alkalkynylcarbonyloxy, phenylcarbonyloxy which is unsubstituted or substituted in the phenyl by one or more radicals selected from the group consisting of halogen, nitro, $(C_1-C_4)$-alkyl, $(C_1-C_4)$-alkoxy, $(C_1-C_4)$-haloalkyl and $(C_1-C_4)$-haloalkoxy; or, is $(C_1-C_6)$-alkylthiocarbonyl, $(C_3-C_6)$-alkenylthio or $(C_3-C_6)$-alkinylthio, $R^8$, $R^9$ independently of one another are $(C_1-C_4)$-alkyl or together are a straight chain or branched $(C_1-C_4)$-alkylene bridge, and $R^{10}$ is H or $(C_1-C_4)$-alkyl.

2. A compound as claimed in claim 1, wherein $R^3$ is $(C_3-C_4)$-alkenyloxy, $(C_3-C_4)$-alkynyloxy, phenyl-$(C_1-C_2)$-alkoxy, in which the phenyl ring is unsubstituted or substituted by one or more radicals selected from the group consisting of halogen, nitro, $(C_1-C_2)$-alkyl, $(C_1-C_2)$-alkoxy, $(C_1-C_2)$-haloalkyl and $(C_1-C_2)$-haloalkoxy; or, is $(C_3-C_4)$-alkenyloxycarbonyl, $(C_3-C_4)$-alkynyloxycarbonyl, phenyl-$(C_1-C_2)$-alkoxycarbonyl, in which the phenyl ring is unsubstituted or substituted by one or more radicals selected from the group consisting of halogen, nitro, $(C_1-C_2)$-alkyl, $(C_1-C_2)$alkoxy, $(C_1-C_2)$-haloalkyl and $(C_1-C_2)$-haloalkoxy; or is $(C_2-C_4)$-alkenylcarbonyl, $(C_2-C_4)$-alkynylcarbonyl, $R^8O—CH(OR^9)—(C_1-C_5)$-alkyl, $(C_1-C_4)$-alkylcarbonyloxy, $(C_3-C_4)$-alkenylcarbonyloxy, ($C_3$–$C_4$)-alkynylcarbonyloxy, phenylcarbonyloxy which is unsubstituted or substituted in the phenyl by one or more radicals selected from the group consisting of halogen, nitro, ($C_1$–$C_4$)-alkyl, ($C_1$–$C_4$)-alkoxy, ($C_1$–$C_4$)-haloalkyl and ($C_1$–$C_4$)-haloalkoxy, and $R^8$, $R^9$ independently of one another are ($C_1$–$C_4$)-alkyl.

3. A compound as claimed in claim 2, wherein $R^3$ is ($C_3$–$C_4$)-alkenyloxy, ($C_3$–$C_4$)-alkynyloxy, benzyloxy, ($C_3$–$C_4$)-alkenyloxycarbonyl or ($C_3$–$C_4$)-alkynyloxycarbonyl.

4. A compound of the formula (I) as claimed in claim 1, wherein $R^1$ and $R^2$ independently of one another are hydrogen or methyl, X ts O, A is ($C_1$–$C_4$)-alkylene or ($C_4$–$C_6$alkenylene.

5. A compound of the formula (I) as claimed in claim 2, wherein $R^1$ and $R^2$ independently of one another are hydrogen or methyl, X is O, A is ($C_1$–$C_4$)-alkylene or ($C_4$–$C_6$)-alkenylene.

6. A compound of the formula (I) as claimed in claim 3, wherein $R^1$ and $R^2$ independently of one another are hydrogen or methyl, X is O, A is ($C_1$–$C_6$)-alkylene or ($C_4$–$C_6$)-alkenylene.

7. A compound as claimed in claim 6, wherein $R^3$ is selected from the group consisting of ($C_3$–$C_4$)-alkenyloxy, ($C_3$–$C_4$)-alkynyloxy, benzyloxy, [trimethylsilyl, triethylsilyl, trimethylsilylmethoxy, 1-(hydroxyimino)-($C_1$–$C_4$)-alkyl, 1-[($C_1$–$C_4$)-alkylimino]-($C_1$–$C_4$)-alkyl, 1-[($C_1$–$C_4$)alkoxyimino]-($C_1$–$C_4$)-alkyl,] ($C_3$–$C_4$)-alkenyloxycarbonyl, and $C_3$–$C_4$)-alkynyloxycarbonyl [and $R^5R^6C$=N—O—, in which $R^5$ and $R^6$, independently of one another are methyl or ethyl or, together with the carbon atom joining them, are cycolpentylidene or cyclohexylidene].

8. A compound of the formula (I) are claimed in claim 7, wherein one of the radicals $R^1$ and $R^2$ is hydrogen and the other is hydrogen or methyl.

9. A compound as claimed in claim 8, wherein —A—$R^3$ is selected from the group consisting of 2-(allyloxy)-ethyl, 3-(allyloxy)-n-propyl, 4-(allyloxy)-n-butyl, 2-allyloxy)-1-methyl-ethyl, 2- (2-methylprop-2-en-1-yl) -ethyl, 2-propargyloxy)-ethyl, 2- (propargyloxy) -1-methyl-ethyl, 3-propargyloxy-propyl, 4-propargyloxybutyl, 2 -benzyloxy-ethyl, allyloxycarbonylmethyl, 1-(allyloxycarbonyl)-1-ethyl, 1-(allyloxycarbonyl)-1,1-dimethylmethyl, propargyloxycarbonylmethyl, and 1-(propargyloxycarbonyl)-1-ethyl, [3-trimethylsilyl-prop-2-en-1-yl, 3-trimethylsilyl-prop-2-yn-1-yl, 3-trimethylsilyl-1-methyl-prop-2-yn-1-yl, 3-trimethylsilyl-1,1-dimethyl-prop-2-yn-1-yl, trimethylsilylmethoxycarbonylmethyl, trimethylsilylmethoxyethyl, trimethylsiloxyethyl, cyclohexylideneaminoxyethyl or -1-(methyl)-ethyl, cyclopentylideneaminooxyethyl or -1-(methyl)-ethyl, 2-propylideneaminooxyethyl or -1-(methyl)-ethyl, 3-pentylideneaminooxyethyl or -1-(methyl)-ethyl, and 2-propylideneaminooxycarbonylmethyl or (2,2-dimethyl-1,3-dioxolan-4-yl)-methyl].

10. A compound as claimed in claim 9, wherein X is O A is $CH_2CH_2$, $CH_2CH_2CH_2$, $CH_2CH_2CH_2CH_2$, $CH_2CH_2CH_2CH_2CH_2$ or $CH(CH_3)CH_2$, and $R^3$ is allyloxy or propargyloxy.

11. A compound as claimed in claim 1, wherein $R^1$ and $R^2$ are hydrogen, X is O, is $CH_2CH_2$ and $R^3$ is allyloxy.

12. A compound as claimed in claim 10, wherein $R^1$ and $R^2$ are hydrogen, X is O, A is $CH_2CH_2CH_2$ and $R^3$ is allyloxy.

13. A compound as claimed in claim 10, wherein $R^1$ and $R^2$ are hydrogen, X is O, A is $CH(CH_3)CH_2$ and $R^3$ is allyloxy.

14. A compound as claimed in claim 9, wherein X is O or NH, A is $CH_2CH_2$ and $R^3$ is 2-propylideneaminooxy or benzoylamido.

* * * * *